United States Patent
Zeller

(12) 
(10) Patent No.: US 6,277,849 B1
(45) Date of Patent: Aug. 21, 2001

(54) N-SULPHONYL AND N-SULPHINYL AMINO ACID AMIDES AS MICROBIOCIDES

(75) Inventor: Martin Zeller, Baden (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/380,024

(22) PCT Filed: Feb. 23, 1998

(86) PCT No.: PCT/EP98/01029

§ 371 Date: Aug. 24, 1999

§ 102(e) Date: Aug. 24, 1999

(87) PCT Pub. No.: WO98/38161

PCT Pub. Date: Sep. 3, 1998

(30) Foreign Application Priority Data

Feb. 25, 1997 (CH) ............................................. 432

(51) Int. Cl.[7] .......................... A01N 41/06; A01N 43/00; C07C 217/60; C07C 237/08; C07C 311/06

(52) U.S. Cl. .......................... 514/248; 514/247; 514/249; 514/256; 514/299; 514/307; 514/311; 514/357; 514/364; 514/365; 514/367; 514/374; 514/378; 514/394; 514/400; 514/406; 514/415; 514/427; 514/438; 514/443; 514/469; 514/473; 514/600; 514/601; 514/605; 544/224; 544/237; 544/257; 544/335; 544/353; 546/122; 546/146; 546/172; 546/332; 546/337; 548/131; 548/178; 548/204; 548/217; 548/236; 548/248; 548/310.1; 548/341.5; 548/362.5; 548/376.1; 548/510; 548/562; 549/58; 549/77; 549/471; 549/479; 564/79; 564/80; 564/97; 564/196; 564/374; 564/381; 564/382

(58) Field of Search .................................. 564/80, 79, 97, 564/99, 196, 374, 381, 382; 514/600, 601, 605, 248, 311, 357, 364, 365, 374, 378, 438, 443; 544/237; 546/332, 337, 171; 548/131, 204, 236, 248; 549/58, 77

(56) References Cited

FOREIGN PATENT DOCUMENTS

WO 95/30651 * 11/1995 (WO).

WO 97/14677 * 4/1997 (WO).

* cited by examiner

Primary Examiner—Richard L. Raymond
(74) Attorney, Agent, or Firm—William A. Teoli, Jr.

(57) ABSTRACT

The invention relates to novel pesticidally active compounds of the general formula I

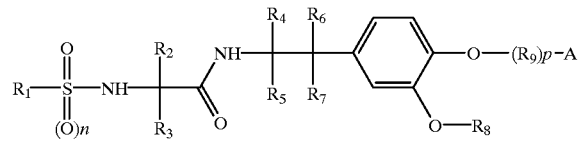

as well as possible isomers and isomeric mixtures thereof, wherein n is a number zero or one; and $R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl, $C_3$–$C_8$acycloalkyl, cyano, $C_1$–$C_6$alkoxycarbonyl, $C_3$–$C_8$alkenyloxycarbonyl, $C_1$–$C_5$alkynyloxycarbonyl; $C_3$–$C_8$cycloalkyl; $C_2$–$C_{12}$alkenyl: $C_2$–$C_{12}$alknyl; $C_1$–$C_{12}$haloalkyl or a group $NR_{11}R_{12}$; wherein $R_{11}$, and $R_{12}$ are each independently of the other hydrogen, $C_1$–$C_6$alkyl or together are tetra- or penta-methylene;

$R_2$ and $R_3$ are each independently of the other hydrogen; $C_1$–$C_8$alkyl; $C_1$–$C_8$alkyl substituted by hydroxy, $C_1$–$C_4$alkoxy, mercapto or by $C_1C_4$alkylthio; $C_3$–$C_8$alkenyl; $C_3$–$C_8$alkynyl; $C_3$–$C_8$cycloalkyl; $C_3$–$C_8$acycloalkyl-$C_1$–$C_4$alkyl or wherein the two groups $R_2$ and $R_3$ together with the carbon atom to which they are bonded form a three- to eight-membered ring;

$R_4$, $R_5$, $R_6$ and $R_7$ are identical or different and are each independently of the others hydrogen or $C_1$–$C_4$alkyl;

$R_8$ is $C_1$–$C_6$alkyl, $C_3$–$C_6$alkenyl or $C_3$–$C_6$alkynyl;

p is a number zero or one;

$R_9$ is $C_1$–$C_6$alkylene; and

A is unsubstituted or mono- or poly-substituted heteroaryl; unsubstituted or mono or poly-substituted aryl containing more than 6 carbon atoms.

The novel compounds have plant-protecting properties and are suitable for the protection of plants against infestation by phytopathogenic microorganisms.

15 Claims, No Drawings

N-SULPHONYL AND N-SULPHINYL AMINO ACID AMIDES AS MICROBIOCIDES

This application is a 371 of international application PCT/EP98/01029, filed Feb. 23, 1998.

The present invention relates to novel a-amino acid derivatives of the formula I below. It relates to the preparation of those substances and to agrochemical compositions comprising at least one of those compounds as active ingredient. The invention relates also to the preparation of the said compositions and to the use of the compounds or the compositions in controlling or preventing the infestation of plants by phytopathogenic microorganisms, especially fungi.

The invention relates to compounds of the general formula I

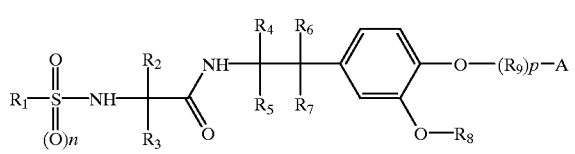

as well as possible isomers and mixtures of isomers thereof, wherein n is a number zero or one; and $R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl, $C_1$–$C_6$alkynyloxycarbonyl; $C_3$–$C_8$cycloalkyl; $C_2$–$C_{12}$alkenyl; $C_2$–$C_{12}$alkynyl; $C_1$–$C_{12}$haloalkyl or a group $NR_{11}R_{12}$; wherein $R_{11}$ and $R_{12}$ are each independently of the other hydrogen, $C_1$–$C_6$alkyl or together are tetra- or penta-methylene;

$R_2$ and $R_3$ are each independently of the other hydrogen; $C_1$–$C_8$alkyl; $C_1$–$C_8$alkyl substituted by hydroxy, $C_1$–$C_4$alkoxy, mercapto or by $C_1$–$C_4$alkylthio; $C_3$–$C_8$alkenyl; $C_3$–$C_8$alkynyl; $C_3$–$C_8$cycloalkyl; $C_3$–$C_8$cycloalkyl-$C_1$–$C_4$alkyl or wherein the two groups $R_2$ and $R_3$ together with the carbon atom to which they are bonded form a three- to eight-membered ring;

$R_4$, $R_5$, $R_6$ and $R_7$ are identical or different and are each independently of the others hydrogen or $C_1$–$C_4$alkyl;

$R_8$ is $C_1$–$C_6$alkyl, $C_3$–$C_6$alkenyl or $C_3$–$C_6$alkynyl;

p is a number zero or one;

$R_9$ is $C_1$–$C_6$alkylene; and

A is unsubstituted or mono- or poly-substituted heteroaryl; unsubstituted or mono- or poly-substituted aryl containing more than 6 carbon atoms.

Examples of aryl in the above-mentioned sense are: naphthyl, anthracenyl, phenanthrenyl.

Examples of heteroaryl are:

furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl, naphthyridinyl.

Examples of substituents of those aryl or heteroaryl groups are:

alkyl, alkenyl, alkynyl, cycloalkyl, cycloalkyl-alkyl, phenyl, phenyl-alkyl, it being possible for those groups to carry one or more identical or different halogen atoms; alkoxy; alkenyloxy; alkynyloxy; alkoxyalkyl; haloalkoxy, alkylthio; haloalkylthio; alkylsulfonyl; formyl; alkanoyl; hydroxy; halogen; cyano; nitro; amino; alkylamino; dialkylamino; carboxy; alkoxycarbonyl; alkenyloxycarbonyl; alkynyloxycarbonyl.

In the above formula I, "halogen" includes fluorine, chlorine, bromine and iodine.

The alkyl, alkenyl and alkynyl radicals may be straight-chain or branched, and this applies also to the alkyl, alkenyl or alkynyl moiety of other alkyl-, alkenyl- or alkynyl-containing groups.

Depending upon the number of carbon atoms mentioned, alkyl on its own or as part of another substituent is to be understood as being, for example, methyl, ethyl, propyl, butyl, pentyl and the isomers thereof, for example isopropyl, isobutyl, tert-butyl or sec-butyl. Cycloalkyl is, depending upon the number of carbon atoms mentioned, cyclopropyl, cyclobutyl, cyclopentyl, cyclohexyl, cycloheptyl or cyclooctyl.

A haloalkyl group may have one or more (identical or different) halogen atoms, for example $CHCl_2$, $CH_2F$, $CCl_3$, $CH_2Cl$, $CHF_2$, $CF_3$, $CH_2CH_2Br$, $C_2Cl_5$, $CH_2Br$, $CHClBr$ etc.

Preference is given to compounds of formula I wherein A is naphthyl, heteroaryl that is formed from one or two five- or six-membered rings and that may contain from 1 to 4 identical or different hetero atoms selected from nitrogen, oxygen and sulfur, wherein that naphthyl or heteroaryl may carry from 1 to 4 identical or different substituents selected from: $C_1$–$C_8$alkyl, $C_2$–$C_8$alkenyl, $C_2$–$C_8$alkynyl, $C_3$–$C_8$cycloalkyl, $C_3$–$C_8$cycloalkyl-$C_1$–$C_4$alkyl, phenyl, phenyl-$C_1$–$C_4$alkyl, it being possible for the hydrogen atoms of those groups to have been replaced by one or more identical or different halogen atoms; $C_1$–$C_8$alkoxy, $C_3$–$C_8$alkenyloxy, $C_3$–$C_8$alkynyloxy, $C_1$–$C_4$alkoxy-$C_1$–$C_4$alkyl, $C_1$–$C_8$haloalkoxy, $C_1$–$C_8$alkylthio, $C_1$–$C_8$haloalkylthio, $C_1$–$C_8$alkylsulfonyl, formyl, $C_2$–$C_8$alkanoyl, hydroxy, halogen, cyano, nitro, amino, $C_1$–$C_8$alkylamino, $C_1$–$C_8$dialkylamino, carboxy, $C_1$–$C_8$alkoxy-carbonyl, $C_3$–$C_8$alkenyloxycarbonyl and $C_3$–$C_8$alkynyloxycarbonyl (sub-group A).

Within the scope of subgroup A, special mention should be made of those compounds of formula I wherein A is naphthyl, furyl, thienyl, pyrrolyl, imidazolyl, pyrazolyl, thiazolyl, oxazolyl, isoxazolyl, oxadiazolyl, thiazolyl, pyridyl, pyridazinyl, pyrimidinyl, pyrazinyl, triazinyl, indolyl, benzothiophenyl, benzofuranyl, benzimidazolyl, benzothiazolyl, benzoxazolyl, quinolinyl, quinoxatinyl, unsubstituted or substituted by from 1 to 3 substituents selected from:

$C_1$–$C_8$alkyl, $C_2$–$C_8$alkenyl, $C_2$–$C_8$alkynyl, $C_3$–$C_8$cycloalkyl, $C_3$–$C_8$cycloalkyl-$C_1$–$C_4$alkyl, phenyl, phenyl-$C_1$–$C_4$alkyl, it being possible for the hydrogen atoms of those groups to have been replaced by one or more identical or different halogen atoms; $C_1$–$C_8$alkoxy, $C_3$–$C_8$alkenyloxy, $C_3$–$C_8$alkynyloxy, $C_1$–$C_4$alkoxy-$C_1$–$C_4$alkyl, $C_1$–$C_8$haloalkoxy, $C_1$–$C_8$alkylthio, $C_1$–$C_8$haloalkylthio, $C_1$–$C_8$alkylsulfonyl, formyl, $C_2$–$C_8$alkanoyl, hydroxy, halogen, cyano, nitro, amino, $C_1$–$C_8$alkylamino, $C_1$–$C_8$dialkylamino, carboxy, $C_1$–$C_8$alkoxycarbonyl, $C_3$–$C_8$alkenyloxycarbonyl and $C_3$–$C_8$alkynyloxycarbonyl (subroup B).

Within the scope of subgroup B, special preference is given to a group of compounds of formula I wherein p is a number one;

A is naphthyl, furyl, thienyl, pyrrolyl, imidazolyl, pyrazolyl, thiazolyl, oxazolyl, isoxazolyl, oxadiazolyl, thiazolyl, pyridyl, pyridazinyl, pyrimidinyl, pyrazinyl, triazinyl, indolyl, benzothiophenyl, benzofuranyl, benzimidazolyl, benzothiazolyl, benzoxazolyl, quinolinyl, quinoxalinyl, unsubstituted or substituted by from 1 to 3 substituents selected from:

$C_1$–$C_8$alkyl, $C_1$–$C_8$haloalkyl, phenyl, phenyl-$C_1$–$C_4$alkyl, $C_1$–$C_8$alkoxy, $C_1$–$C_8$haloalkoxy, $C_1$–$C_8$alkylthio, $C_1$–$C_8$haloalkylthio, halogen, cyano and nitro (sub-group Ca).

A special group within the scope of sub-group Ca comprises compounds of formula I wherein
$R_9$ is —$CH_2$—;
A is naphthyl, furyl, thienyl, thiazolyl, oxazolyl, pyridyl. pyridazinyl, pyrimidinyl, pyrazinyl, triazinyl, unsubstituted or substituted by from 1 to 3 substituents selected from:

$C_1$–$C_8$alkyl, $C_1$–$C_8$haloalkyl, phenyl, phenyl-$C_1$–$C_4$alkyl, $C_1$–$C_8$alkoxy, $C_1$–$C_8$haloalkoxy, $C_1$–$C_8$alkylthio, $C_1$–$C_8$haloalkylthio, halogen, cyano and nitro (sub-group Cb).

Another especially preferred group within the scope of sub-group B comprises compounds of formula I wherein
n is a number one,
$R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl; $C_2$–$C_{12}$alkenyl; $C_2$–$C_{12}$alkynyl; $C_1$–$C_{12}$haloalkyl or a group $NR_{11}R_{12}$;
wherein $R_{11}$ and $R_{12}$ are each independently of the other hydrogen, $C_1$–$C_6$alkyl or together are tetra- or pentamethylene;
$R_2$ is hydrogen;
$R_3$ is $C_1$–$C_8$alkyl;
$C_1$–$C_8$alkyl substituted by hydroxy, $C_1$–$C_4$alkoxy, mercapto or by $C_1$–$C_4$alkylthio; $C_3$–$C_8$alkenyl; $C_3$–$C_8$alkynyl; $C_3$–$C_8$cycloalkyl; $C_3$–$C_8$cycloalkyl-$C_1$–$C_4$alkyl (sub-group Da).

Within group Da, preference is given to compounds of formula I wherein
$R_1$ is $C_1$–$C_{12}$alkyl, $C_1$–$C_{12}$haloalkyl or a group $NR_{11}R_{12}$; wherein $R_{11}$ and $R_{12}$ are each independently of the other $C_1$–$C_6$alkyl;
$R_3$ is $C_1$–$C_8$alkyl;
$R_4$ is hydrogen or $C_1$–$C_4$alkyl;
$R_5$, $R_6$ and $R_7$ are hydrogen;
$R_8$ is $C_1$–$C_6$alkyl (sub-group Db).

A preferred group within the scope of sub-group Db comprises those compounds of formula I wherein
$R_1$ is $C_1$–$C_4$alkyl or dimethylamino;
$R_3$ is $C_3$–$C_4$alkyl;
$R_4$ is hydrogen or methyl;
$R_8$ is $C_1$–$C_2$alkyl (sub-group Dc).

A special group within the scope of sub-group Dc is formed by compounds of formula I wherein
$R_3$ is 2-propyl;
$R_4$ is hydrogen;
$R_8$ is methyl (sub-group Dd).

The presence of at least one asymmetric carbon atom and/or at least one asymmetric sulfur atom in the compounds of formula I means that the compounds may occur in optically isomeric forms. As a result of the presence of a possible aliphatic C=C double bond, geometric isomerism may also occur. The formula I is intended to include all those possible isomeric forms and mixtures thereof.

Certain α-amino acid derivatives having a different kind of structure have already been proposed for controlling plant-destructive fungi (for example in EP-398 072, EP425 925, DE4 026 966, EP477 639, EP493 683, DE-4 035 851, EP487 154, EP-496 239, EP-550 788 and EP-554 729).

Those preparations are not satisfactory, however, in respect of their action. Surprisingly, with the compound structure of formula I, new kinds of microbicides having a high level of activity have been found.

The compounds of formula I can be prepared as follows:
a) by reaction of a substituted amino acid of formula II

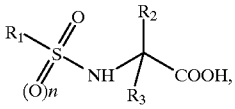

wherein the radicals $R_1$, $R_2$ and $R_3$ and n are as defined above, or a carboxy-activated derivative thereof, if desired in the presence of a catalyst, if desired in the presence of an acid-binding agent and if desired in the presence of a diluent, with an amine of formula III

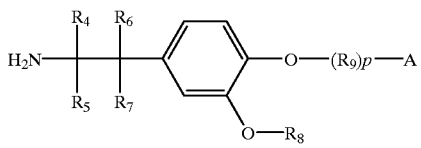

wherein $R_4$, $R_5$, $R_6$, $R_7$, $R_8$, $R_9$, p and A are as defined above.

The amino acid derivatives of formula II required for carrying out Process a) according to the invention are known per se or can be prepared in accordance with Process aa) described below.

The amines of formula III are novel and the invention relates also thereto.

The amines of formula III can be prepared in accordance with Process bb) described below.

Suitable carboxy-activated derivatives of the amino acid of formula II include any carboxy-activated derivatives, such as acid halides, for example acid chlorides; also symmetrical or mixed anhydrides, for example the mixed O-alkylcarboxylic acid anhydrides; and also activated esters, for example p-nitrophenyl esters or N-hydroxysuccinimide esters, and activated forms of the amino acid produced in situ using condensation agents, e.g. dicyclohexylcarbodiimide, carbonyldiimidazole, O-(benzotriazol-1-yl)-N,N,N',N'-bis(pentaethylene)uronium hexafluorophosphate, O-(benzotriazol-1-yl)-N,N,N',N'-bis(tetramethylene)uronium hexafluorophosphate, (benzotriazol-1-yloxy)-tripyrrolidinophosphonium hexafluorophosphate, (benzotriazol-1-yloxy)-tris (dimethylamino)phosphonium hexafluorophosphate or O-(benzotriazol-1-yl)-N,N,N',N'-tetramethyluronium hexafluorophosphate.

The acid halides corresponding to the amino acid of formula II can be prepared by reacting the amino acid of formula II in a generally known manner with a halogenating agent, for example phosphorus pentachloride, thionyl chloride or oxalyl chloride.

The mixed anhydrides corresponding to the amino acid of formula II can be prepared by reacting the amino acid of formula II with a chloroformic acid ester, for example a chloroformic acid alkyl ester, preferably isobutyl chloroformate, if desired in the presence of an acid-binding agent, such as an inorganic or organic base, for example a tertiary amine, e.g. triethylamine, pyridine, N-methylpiperidine or N-methylmorpholine.

The reaction of the amino acid of formula II, or of a carboxy-activated derivative of the amino acid of formula II, with an amine of formula III is carried out in an inert diluent, such as an aromatic, non-aromatic or halogenated hydrocarbon, for example a chlorinated hydrocarbon, e.g. methylene chloride or toluene; a ketone, e.g. acetone; an ester, e.g. ethyl acetate; an amide, e.g. dimethylformamide; a nitrile, e.g. acetonitrile; or an ether, e.g. tetrahydrofuran, dioxane, diethyl ether or tert-butyl methyl ether; or in a mixture of those inert diluents, if desired in the presence of an acid-binding agent, such as an inorganic or organic base, for example a tertiary amine, e.g. triethylamine, pyridine, N-methylpiperidine or N-methyl-morpholine, at temperatures of from −80 to +150° C., preferably from −40 to +40° C.

b) by oxidation of a compound of formula I'

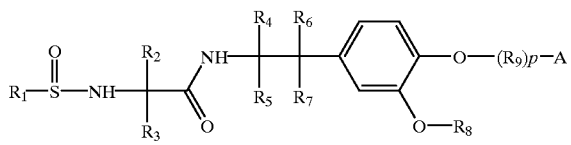

wherein $R_4$, $R_5$, $R_6$, $R_7$, $R_8$, $R_9$, p and A are as defined above, with the proviso that none of the substituents $R_1$, $R_2$, $R_3$ and A contains a thiol or alkylthio group.

Suitable oxidising agents include both organic oxidising agents, such as alkyl hydro-peroxides, for example cumyl hydroperoxide, and inorganic oxidising agents, such as peroxides, for example hydrogen peroxide, and transition metal oxides, for example chromium trioxide, and transition metal oxide salts, for example potassium permanganate, potassium dichromate or sodium dichromate.

The reaction of a compound of formula I' with the oxidising agent is carried out in an inert diluent, such as water or a ketone, for example acetone, or in a mixture of those inert diluents, optionally in the presence of an acid or optionally in the presence of a base, at temperatures of from −80 to +150° C.

c) by reaction of a compound of formula IV

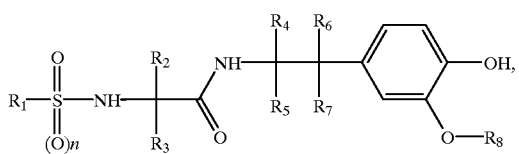

wherein n, $R_1$, $R_2$, $R_3$, $R_4$, $R_5$, $R_6$, $R_7$ and $R_8$ are as defined above, with a compound of formula V

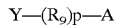    V wherein $R_9$, p and A are as defined above and wherein Y is a leaving group. Suitable leaving groups include halides, for example chlorides or bromides, and sulfonates, for example tosylates, mesylates or triflates.

The reaction of the compounds of formula IV with compounds of formula V is carried out in an inert diluent. The following may be mentioned as examples: aromatic, non-aromatic or halogenated hydrocarbons, e.g. toluene or methylene chloride; ketones, e.g. acetone; esters, e.g. ethyl acetate; amides, e.g. dimethylformamide; nitrites, e.g. acetonitrile; ethers, e.g. tetrahydrofuran; dioxane, diethyl ether or tert-butyl methyl ether; alcohols, e.g. methanol, ethanol, n-butanol, isopropanol or tert-butanol; dimethyl sulfoxide; or water; or mixtures of those inert diluents. The reaction of the compounds of formula IV with compounds of formula V is carried out if desired in the presence of an acid-binding agent. Suitable acid-binding agents include inorganic or organic bases, for example alkali metal or alkaline earth metal hydroxides, alcoholates or carbonates, e.g. sodium hydroxide, potassium hydroxide, sodium methanolate, potassium methanolate, sodium ethanolate, potassium ethanolate, sodium tert-butanolate, potassium tert-butanolate, sodium carbonate or potassium carbonate. The temperatures are from −80 to +200° C., preferably from 0 to +120° C.

The compounds of formula IV can be prepared in accordance with Process cc).

d) by reaction of a sulfonic acid or sulfinic acid, or of a sulfonic acid or sulfinic acid derivative, of formula VI

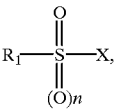

wherein $R_1$ and n are as defined above and wherein X is an OH group or a leaving group, respectively, with an amine of formula VII

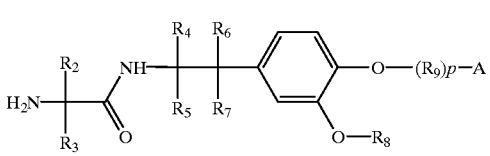

wherein $R_2$, $R_3$, $R_4$, $R_5$, $R_6$, $R_7$, $R_8$, $R_9$, p and A are as defined above.

The invention relates also to the compounds of formula VII and to their preparation.

The sulfonic acid or sulfinic acid, or sulfonic acid or sulfinic acid derivatives, of formula VI required for Process d) are known per se. The amines of formula VII also required are novel and the invention relates also thereto; they can be prepared in accordance with Process dd) below.

Suitable sulfonic acid or sulfinic acid derivatives of formula VI include any compounds wherein X is a leaving group, such as sulfonic acid halides or sulfinic acid halides, e.g. sulfochlorides or sulfinic acid chlorides; also symmetrical of mixed anhydrides; and also activated forms of sulfonic acid or sulfinic acid produced in situ using condensation agents, such as dicyclohexylcarbodiimide or carbonyldiimidazole.

The reaction of the sulfonic acid or sulfinic acid, or of the sulfonic acid or sulfinic acid derivative, of formula VI with an amine of formula VII is carried out in an inert diluent, such as an aromatic, non-aromatic or halogenated hydrocarbon, for example a chlorinated hydrocarbon, e.g. methylene chloride or toluene; a ketone, e.g. acetone; an ester, e.g. ethyl acetate; an amide, e.g. dimethylformamide; a nitrile, e.g. acetonitrile; or an ether, e.g. tetrahydrofuran, dioxane, diethyl ether or tert-butyl methyl ether; or water; or in a mixture of those inert diluents, if desired in the presence of an acid-binding agent, such as an inorganic or organic base; for example an alkali metal or alkaline earth metal hydroxide or carbonate, e.g. sodium hydroxide, potassium hydroxide, sodium carbonate or potassium carbonate, or, for example, a tertiary amine, e.g. triethylamine, pyridine, N-methylpiperidine or N-methyl-morpholine, at temperatures of from −80 to +150° C., preferably from −20 to +60° C.

aa) The required amino acid derivatives of formula II can be prepared by reaction of an amino acid of formula VIII

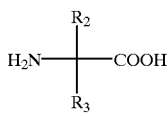
VIII with a sulfonic acid or sulfinic acid, or with a sulfonic acid or sulfinic acid derivative, of formula VI

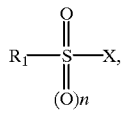
VI wherein $R_1$, $R_2$, $R_3$ and n are as defined above and wherein X is an OH group pr a leaving group, respectively.

The sulfonic acid or sulfinic acid, or sulfonic acid or sulfinic acid derivative, of formula VI required for Process aa) and the amino acids of formula VIII are known per se.

Suitable sulfonic acid or sulfinic acid derivatives of formula VI include any compounds wherein X is a leaving group, such as sulfonic acid halides or sulfinic acid halides, e.g. sulfochlorides or sulfinic acid chlorides; also symmetrical or mixed anhydrides; and also activated forms of sulfonic acid or sulfinic acid produced in situ using condensation agents, such as dicyclohexylcarbodiimide or carbonyldiimidazole.

The reaction of the sulfonic acid or sulfinic acid, or of the sulfonic acid or sulfinic acid derivative, of formula VI with an amine of formula VIII is carried out in an inert diluent, such as an aromatic, non-aromatic or halogenated hydrocarbon, for example a chlorinated hydrocarbon, e.g. methylene chloride or toluene; a ketone, e.g. acetone; an ester, e.g. ethyl acetate; an amide, e.g. dimethylformamide; a nitrile, e.g. acetonitrile; or an ether, e.g. tetrahydrofuran, dioxane, diethyl ether or tert-butyl methyl ether; or water; or in a mixture of those inert diluents, if desired in the presence of an acid-binding agent, such as an inorganic or organic base; for example an alkali metal or alkaline earth metal hydroxide or carbonate, e.g. sodium hydroxide, potassium hydroxide, sodium carbonate or potassium carbonate, or, for example, a tertiary amine, e.g. triethylamine, pyridine, N-methylpiperidine or N-methyl-morpholine, at temperatures of from −80 to +150° C., preferably from −20 to +60° C.

bb) The amines of formula III can be prepared in accordance with the following process variants:

Process variant 1 (for $R_4$, $R_5$, $R_6$ and $R_7$ = hydrogen)

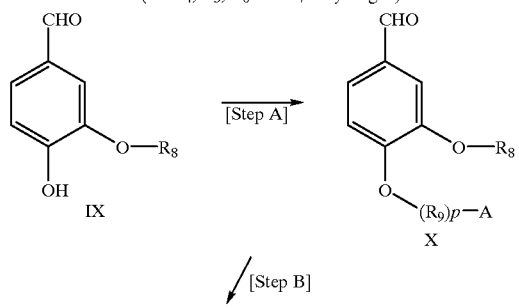

Process variant 2

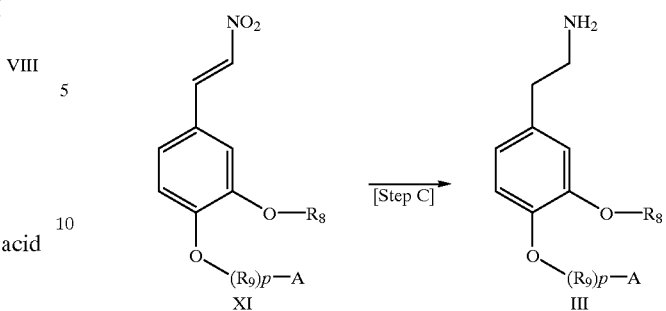

Process variant 3

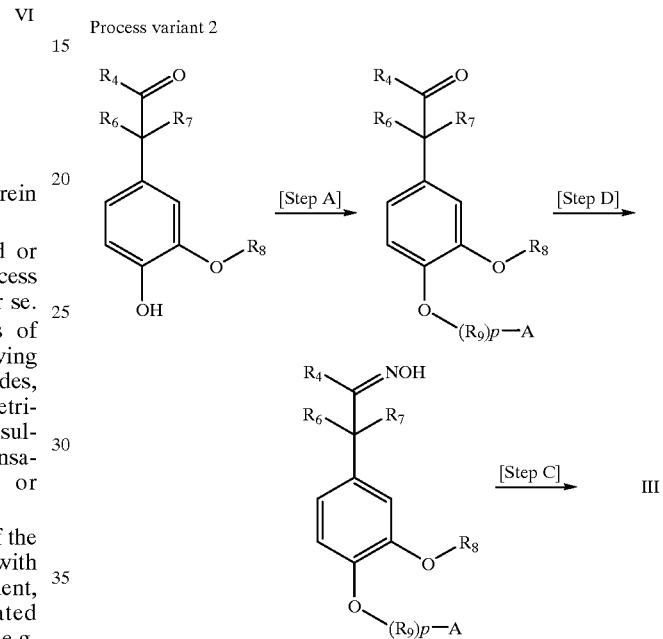

Process variant 4

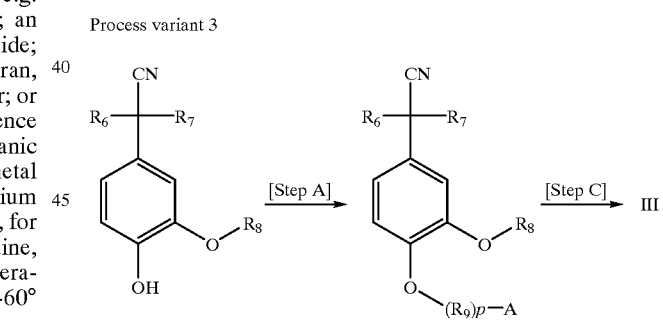

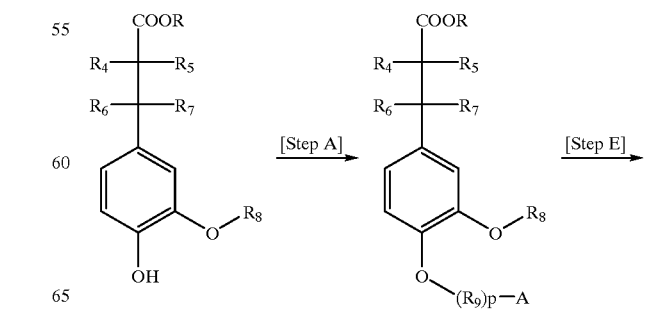

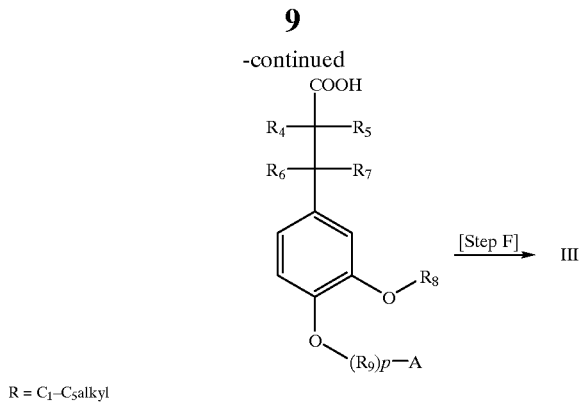

R = $C_1$–$C_5$alkyl

Step A comprises the alkylation of a phenol with a compound of formula V. The reaction is carried out as described under Process c).

Step B comprises the reaction of an aromatic aldehyde with nitromethane. The reaction of the two reactants is carried out in an inert diluent, such as an organic carboxylic acid, for example acetic acid, optionally in the presence of the ammonium salt of that carboxylic acid, for example ammonium acetate, at temperatures of from 0° to +200° C.

Step C comprises the reduction of an unsaturated nitrogen compound. The reaction is carried out in an inert diluent, such as an ether, for example diethyl ether, dioxane or tetrahydrofuran, or an alcohol, for example methanol, ethanol or isopropanol, with a boron hydride, a boron hydride complex, for example the complex of boron hydride and tetrahydrofuran, an alkali metal borohydride, alkali metal aluminium hydride, for example lithium aluminium hydride, or an aluminium alkoxyhydride, or with hydrogen optionally in the presence of a transition metal or a transition metal compound, for example nickel, at temperatures of from −50° to +250° C.

Step D comprises the reaction of an aldehyde or a ketone with hydroxylamine or a hydroxylamine salt. The reaction is carried out in an inert diluent, such as an alcohol, for example methanol, ethanol or isopropanol, an ether, for example diethyl ether, dioxane or tetrahydrofuran, an amide, for example dimethylformamide, or in water, or in a mixture of those inert diluents, optionally in the presence of an organic or inorganic base, such as a tertiary amine, for example triethylamine, a nitrogen-containing heteroaromatic compound, for example pyridine, an alkali or alkaline earth metal carbonate or hydrogen carbonate, for example sodium carbonate or potassium carbonate, at temperatures of from −20° to +150° C.

Step E comprises the hydrolysis of a lower alkyl ester. The reaction is carried out in an inert diluent, such as an alcohol, for example methanol, ethanol or isopropanol, an ether, for example diethyl ether, dioxane or tetrahydrofuran, a halogenated hydrocarbon, for example dichloromethane, or in water or in a mixture of those inert diluents, optionally in the presence of a base, such as an alkali or alkaline earth metal hydroxide, for example lithium hydroxide, sodium hydroxide or potassium hydroxide, or in the presence of an acid, for example sulfuric acid, hydrochloric acid or trifluoroacetic acid, at temperatures of from −20° to +160° C.

Step F comprises the reaction of a carboxylic acid or an activated derivative of that carboxylic acid with hydrazoic acid or with a salt of that acid. Suitable carboxy-activated derivatives include any carboxy-activated derivatives, such as acid halides, for example acid chlorides; and also symmetric or mixed anhydrides, for example the mixed O-alkylcarboxylic acid anhydrides. Suitable salts of hydrazoic acid include, for example, alkali or alkaline earth metal azides, for example sodium azide. The reaction is carried out in a diluent, such as a hydrocarbon, for example toluene or xylene, a halogenated hydrocarbon, for example chloroform, an ether, for example dioxane, a ketone, for example acetone or methyl ethyl ketone, an alcohol, for example tert-butanol, or in water, or in a mixture of those diluents, optionally in the presence of an acid, such as an inorganic acid, for example sulfuric acid or hydrochloric acid, at temperatures of from 40° to +200° C.

cc) The compounds of formula IV can be prepared by reaction of a substituted amino acid of formula II

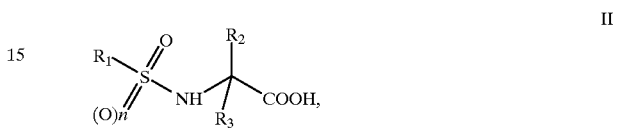

wherein the radicals $R_1$, $R_2$ and $R_3$ and n are as defined above, or a carboxy-activated derivative thereof, if desired in the presence of a catalyst, if desired in the presence of an acid-binding agent and if desired in the presence of a diluent, with a compound of the general formula XII, or an acid addition salt of that compound,

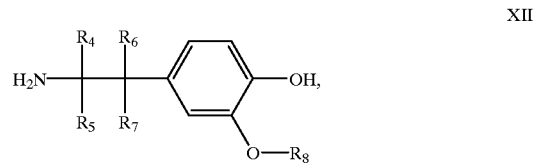

wherein $R_4$, $R_5$, $R_6$, $R_7$ and $R_8$ are as defined above.

Suitable carboxy-activated derivatives of the amino acid of formula II include any carboxy-activated derivatives, such as acid halides, for example acid chlorides; also symmetrical or mixed anhydrides, for example the mixed O-alkylcarboxylic acid anhydrides; and also activated esters, for example p-nitrophenyl esters or N-hydroxysuccinimide esters, and activated forms of the amino acid produced in situ using condensation agents, e.g. dicyclohexylcarbodiimide, carbonyldiimidazole, O-(benzotriazol-1-yl)-N,N,N',N'-bis(pentamethylene)uronium hexafluorophosphate, O-(benzotriazol-1-yl)-N,N,N',N'-bis(tetramethylene)uronium hexafluorophosphate, (benzotriazol-1-yloxy)-tripyrrolidinophosphonium hexafluorophosphate, (benzotriazol-1-yloxy)-tris(dimethylamino)phosphonium hexafluorophosphate or O-(benzotriazol-1-yl)-N,N,N',N'-tetramethyluronium hexafluorophosphate.

The acid halides corresponding to the amino acid of formula II can be prepared by reacting the amino acid of formula II in a generally known manner with a halogenating agent, for example phosphorus pentachloride, thionyl chloride or oxalyl chloride.

The mixed anhydrides corresponding to the amino acid of formula II can be prepared by reacting the amino acid of formula II with a chloroformic acid ester, for example a chloroformic acid alkyl ester, preferably isobutyl chloroformate, if desired in the presence of an acid-binding agent, such as an inorganic or organic base, for example a tertiary amine, e.g. triethylamine, pyridine, N-methylpiperidine or N-methylmorpholine.

The reaction of the amino acid of formula II, or of a carboxy-activated derivative of the amino acid of formula II, with a compound of the general formula XII is carried out in an inert diluent, such as an aromatic, non-aromatic or halogenated hydrocarbon, for example a chlorinated hydrocarbon, e.g. methylene chloride or toluene; a ketone, e.g. acetone; an ester, e.g. ethyl acetate; an amide, e.g. dimethylformamide; a nitrile, e.g. acetonitrile; or an ether, e.g. tetrahydrofuran, dioxane, diethyl ether or tert-butyl methyl ether; or in a mixture of those inert diluents, if desired in the presence of an acid-binding agent, e.g. an inorganic or organic base, for example a tertiary amine, e.g. triethylamine, pyridine, N-methylpiperidine or N-methylmorpholine, at temperatures of from −80 to +150° C., preferably from −40 to +40° C.

dd) The required amines of formula VII can be prepared in accordance with the following reaction sequence

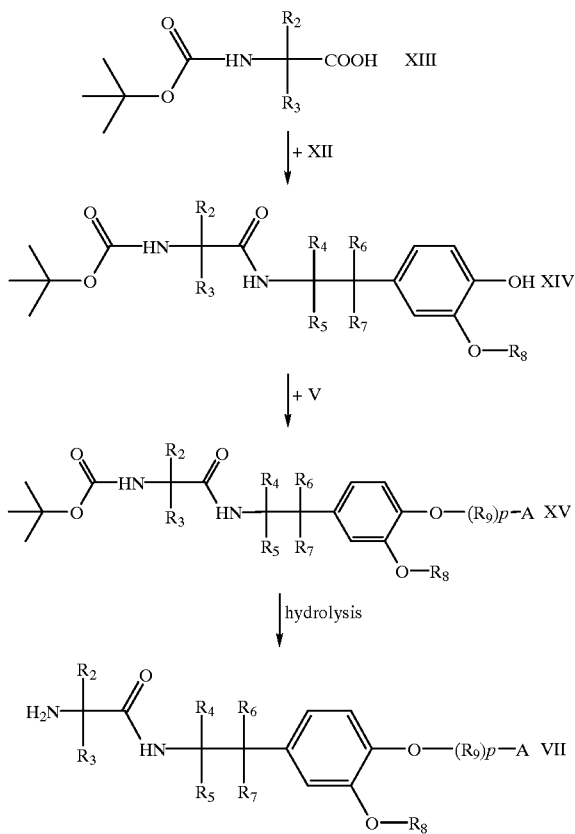

In a first step, an amino acid derivative of the general formula XIII, or a carboxy-activated derivative thereof, is reacted, if desired in the presence of a catalyst, if desired in the presence of an acid-binding agent and if desired in the presence of a diluent, with an amine of the general formula XII.

Suitable carboxy-activated derivatives of the amino acid of formula XIII include any carboxy-activated derivatives, such as acid halides, for example acid chlorides; also symmetrical or mixed anhydrides, for example the mixed O-alkylcarboxylic acid anhydrides; and also activated esters, for example p-nitrophenyl esters or N-hydroxysuccinimide esters, and activated forms of the amino acid produced in situ using condensation agents, e.g. dicyclohexylcarbodiimide, carbonyldiimidazole, O-(benzotriazol-1-yl)-N,N,N',N'-bis(pentamethylene) uronium hexafluorophosphate, O-(benzotriazol-1-yl)-N,N, N',N'-bis(tetramethylene)uronium hexafluorophosphate, (benzotriazol-1-yloxy)-tripyrrolidinophosphonium hexafluorophosphate, (benzotriazol-1-yloxy)tris (dimethylamino)phosphonium hexafluorophosphate or O-(benzotriazol-1-yl)-N,N,N',N'-tetramethyluronium hexafluorophosphate.

The acid halides corresponding to the amino acid of formula XIII can be prepared by reacting the amino acid of formula XIII in a generally known manner with a halogenating agent, for example phosphorus pentachloride, thionyl chloride or oxalyl chloride.

The mixed anhydrides corresponding to the amino acid of formula XIII can be prepared by reacting the amino acid of formula XIII with a chloroformic acid ester, for example a chloroformic acid alkyl ester, preferably isobutyl chloroformate, if desired in the presence of an acid-binding agent, such as an inorganic or organic base, for example a tertiary amine, e.g. triethylamine, pyridine, N-methylpiperidine or N-methylmorpholine.

The reaction of the amino acid of formula XIII, or of a carboxy-activated derivative of the amino acid of formula XIII, with an amine of formula XII is carried out in an inert diluent, such as an aromatic, non-aromatic or halogenated hydrocarbon, for example a chlorinated hydrocarbon, e.g methylene chloride or toluene; a ketone, e.g. acetone; an ester, e.g. ethyl acetate; an amide, e.g. dimethylformamide; a nitrile, e.g. acetonitrile; or an ether, e.g. tetrahydrofuran, dioxane, diethyl ether or tert-butyl methyl ether; or in a mixture of those inert diluents, if desired in the presence of an acid-binding agent, e.g. an inorganic or organic base, for example a tertiary amine, e.g. triethylamine, pyridine, N-methylpiperidine or N-methylmorpholine, at temperatures of from −80 to +150° C., preferably from 40 to +40° C.

In a second step, a compound of formula XIV is reacted with a compound of formula V.

The reaction of a compound of formula XIV with a compound of formula V is carried out in an inert diluent. The following may be mentioned as examples: aromatic, non-aromatic or halogenated hydrocarbons, for example toluene or methylene chloride; ketones, for example acetone; esters, for example ethyl acetate; amides, for example dimethylformamide; nitriles, for example acetonitrile; ethers, for example tetrahydrofuran, dioxane, diethyl ether or tertbutyl methyl ether; alcohols, for example methanol, ethanol, n-butanol, isopropanol or tertbutanol; dimethyl sulfoxide or water or mixtures of those inert diluents. The reaction of the compounds of formula XIV with compounds of formula V is carried out if desired in the presence of an acid-binding agent. Suitable acid-binding agents include inorganic or organic bases, for example alkali or alkaline earth metal hydroxides, alcoholates or carbonates, e.g. sodium hydroxide, potassium hydroxide, sodium methanolate, potassium methanolate, sodium ethanolate, potassium ethanolate, sodium tert-butanolate, potassium tert-butanolate, sodium carbonate or potassium carbonate. The temperatures are from −80 to +200° C., preferably from 0 to 120° C.

In a third step, compounds of formula XV are subjected to acid hydrolysis. The reaction of a compound of formula XV with an inorganic or organic acid, for example a mineral acid, e.g. hydrochloric acid or sulfuric acid, or a carboxylic acid, e.g. acetic acid or trifluoroacetic acid, or a sulfonic acid, e.g. methanesulfonic acid or p-toluenesulfonic acid, is carried out if desired in an inert diluent, such as an aromatic, non-aromatic or halogenated hydrocarbon, for example a chlorinated hydrocarbon, e.g. methylene chloride or toluene; a ketone, e.g. acetone; an ester, e.g. ethyl acetate; an ether, e.g. tetrahydrofuran or dioxane; or water, at temperatures of from −40 to +150° C. If desired, it is also possible to use mixtures of different acids and of different inert diluents, or the acid itself may serve as the diluent.

The compounds of formula I are oils or solids at room temperature that are distinguished by valuable microbicidal properties. They can be used in the agricultural sector or related fields preventively and curatively in the control of plant-destructive microorganisms. The compounds of formula I according to the invention are distinguished at low rates of concentration not only by outstanding microbicidal, especially fungicidal, activity but also by being especially well tolerated by plants.

Surprisingly, it has now been found that the compounds of formula I have for practical purposes a very advantageous biocidal spectrum in the control of phytopathogenic microorganisms, especially fungi. They possess very advantageous curative and preventive properties and are used in the protection of numerous crop plants. With the compounds of formula I it is possible to inhibit or destroy pests that occur on various crops of useful plants or on parts of such plants (fruit, blossom, leaves, stems, tubers, roots), while parts of the plants which grow later also remain protected, for example, against phytopathogenic fungi.

The novel compounds of formula I prove to be effective against specific genera of the fungus class Fungi imperfecti (e.g. Cercospora), Basidiomycetes (e.g. Puccinia) and Ascomycetes (e.g. Erysiphe and Venturia) and especially against Oomycetes (e.g. Plasmopara, Peronospora, Pythium and Phytophthora). They therefore represent in plant protection a valuable addition to the compositions for controlling phytopathogenic fungi. The compounds of formula I can also be used as dressings for protecting seed (fruit, tubers, grains) and plant cuttings from fungal infections and against phytopathogenic fungi that occur in the soil.

The invention relates also to compositions comprising compounds of formula I as active ingredient, especially plant-protecting compositions, and to the use thereof in the agricultural sector or related fields.

In addition, the present invention includes the preparation of those compositions, wherein the active ingredient is homogeneously mixed with one or more of the substances or groups of substances described herein. Also included is a method for the treatment of plants which comprises the application of the novel compounds of formula I or the novel compositions.

Target crops to be protected within the scope of this invention comprise, for example, the following species of plants: cereals (wheat, barley, rye, oats, rice, maize, sorghum and related species); beet (sugar beet and fodder beet); pomes, stone fruit and soft fruit (apples, pears, plums, peaches, almonds, cherries, strawberries, raspberries and blackberries), leguminous plants (beans, lentils, peas, soybeans); oil plants (rape, mustard, poppy, olives, sunflowers, coconut, castor oil plants, cocoa beans, groundnuts); cucurbitaceae (marrows, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) and plants such as tobacco, nuts, coffee, sugar cane, tea, pepper, vines, hops, bananas and natural rubber plants, and also ornamentals.

The compounds of formula I are normally applied in the form of compositions and can be applied to the area or plant to be treated simultaneously or in succession with other active ingredients. Those further active ingredients may be fertilisers, micronutrient donors or other preparations that influence plant growth. It is also possible to use selective herbicides or insecticides, fungicides, bactericides, nematicides, molluscicides or mixtures of several of those preparations, if desired together with further carriers, surfactants or other application-promoting adjuvants customarily employed in formulation technology.

The compounds of formula I can be mixed with other fungicides, with the result that in some cases unexpected synergistic effects are obtained. Especially preferred mixing partners are azoles, such as propiconazole, difenoconazole, cyproconazole, epoxiconazole, tebuconazole, tetraconazole, fenbuconazole, metconazole, bromuconazole; also fenpropidine, fenpropimorph, cyprodinil, pyrimethanil, benzo-1,2,3thiadiazole-7-carbonothioic acid S-methyl ester, and strobilurins, such as azoxystrobin and cresoxime-methyl.

Suitable carriers and surfactants may be solid or liquid and correspond to the substances ordinarily employed in formulation technology, such as, e.g. natural or regenerated mineral substances, solvents, dispersants, wetting agents, tackifiers, thickeners, binders or fertilisers.

A preferred method of applying a compound of formula I, or an agrochemical composition comprising at least one of those compounds, is application to the foliage (foliar application), the frequency and the rate of application depending upon the risk of infestation by the pathogen in question. The compounds of formula I may also be applied to seed grains (coating) either by impregnating the seeds with a liquid formulation of the active ingredient or by coating them with a solid formulation.

The compounds of formula I are used in unmodified form or, preferably, together with the adjuvants conventionally employed in formulation technology, and are for that purpose advantageously formulated in known manner e.g. into emulsifiable concentrates, coatable pastes, directly sprayable or dilutable solutions, dilute emulsions, wettable powders, soluble powders, dusts, granules, and by encapsulation in e.g. polymer substances. As with the nature of the compositions, the methods of application, such as spraying, atomising, dusting, scattering, coating or pouring, are chosen in accordance with the intended objectives and the prevailing circumstances.

Advantageous rates of application are normally from 1 g to 2 kg of active ingredient (a.i.) per hectare (ha), preferably from 10 g to 1 kg a.i./ha, especially from 25 g to 750 g a.i./ha. When used as seed dressings, rates of from 0.001 g to 1.0 g of active ingredient per kg of seed are advantageously used.

The formulations, i.e. the compositions, preparations or mixtures comprising the corn-pound(s) (active ingredient (s)) of formula I and, where appropriate, a solid or liquid adjuvant, are prepared in known manner, e.g. by homogeneously mixing and/or grinding the active ingredient with extenders and adjuvants customary in agricultural technology, e.g. solvents, solid carriers and, where appropriate, surface-active compounds (surfactants).

Further surfactants customarily used in formulation technology will be known to the person skilled in the art or can be found in the relevant technical literature.

The agrochemical compositions usually comprise 0.01 to 99% by weight, preferably 0.1 to 95% by weight, of a compound of formula I, 99.99 to 1% by weight, preferably 99.9 to 5% by weight, of a solid or liquid adjuvant, and 0 to 25% by weight, preferably 0.1 to 25% by weight, of a surfactant.

Whereas commercial products will preferably be formulated as concentrates, the end user will normally employ dilute formulations.

The compositions may also comprise further ingredients, such as stabilisers, antifoams, viscosity regulators, binders and tackifiers, as well as fertilisers or other active ingredients for obtaining special effects.

The Examples which follow illustrate the invention described above, without limiting the scope thereof in any way. Temperatures are given in degrees Celsius.

PREPARATION EXAMPLES FOR COMPOUNDS OF FORMULA I:

Example 1.1

(S)-2Methylsulfonyl-amino)-3methyl-butyric acid N-{2-[3-methoxy-4-(naphthalen-1-ylmethoxy)-phenyl]-ethyl}-amide

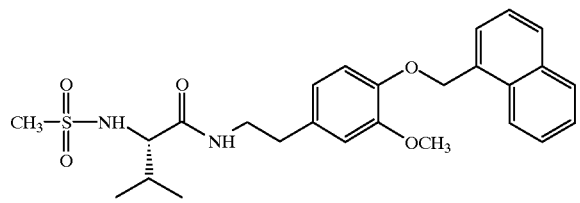

A mixture of 1.3 g of (S)-methanesulfonic acid N-(2-methyl-1-carboxy)-propylamide, 2.0 g of 2-[3-methoxy-4-(naphthalen-1-ylmethoxy)-phenyl]-ethylamine, 2.9 g of (benzotriazol-1-yl-oxy)-tris(dimethylamino)phosphonium hexafluorophosphate and 3.4 ml of N-ethyl-diisopropylamine is stirred in 30 ml of N,N-dimethylformamide at room temperature for 2 hours. The reaction mixture is introduced into 300 ml of water. Extraction is carried out twice using 300 ml of ethyl acetate each time. The organic phases are washed once with 100 ml of saturated sodium chloride solution, combined, dried over magnesium sulfate and concentrated, yielding (S)-2-(methylsulfonyl-amino)-3-methyl-butyric acid N-{2-[3-methoxy-4-(naphthalen-1-ylmethoxy)-phenyl]-ethyl}-amide, which can be purified by chromatography on silica gel with ethyl acetate/n-hexane=2:1 and recrystallisation from ethyl acetate/n-hexane. M.p. 153–157° C.

The Examples listed in Table 1 are obtained in an analogous manner.

TABLE 1

| Comp. No. | Conf. at α-C | $R_1$ | $R_2$ | $R_3$ | Phys. data m.p. °C. |
|---|---|---|---|---|---|
| 1.1 | (S) | methyl | 2-propyl | —CH₂-(naphthalen-1-yl) | 153–157 |
| 1.2 | (S) | N(CH₃)₂ | 2-propyl | —CH₂-(naphthalen-1-yl) | oil |
| 1.3 | (S) | n-propyl | 2-propyl | —CH₂-(naphthalen-1-yl) | |
| 1.4 | (S) | 3-Cl-propyl | 2-propyl | —CH₂-(naphthalen-1-yl) | 134–138 |

TABLE 1-continued

[Structure: R₁-SO₂-NH-C(R₂)H-C(=O)-NH-CH₂CH₂-phenyl(4-OR₃, 3-OCH₃)]

| Comp. No. | Conf. at α-C | R₁ | R₂ | R₃ | Phys. data m.p. °C. |
|---|---|---|---|---|---|
| 1.5 | (S) | n-butyl | 2-propyl | —CH₂-(1-naphthyl) | |
| 1.6 | (S) | methyl | 2-Me-2-propyl | —CH₂-(1-naphthyl) | |
| 1.7 | (S) | ethyl | 2-Me-2-propyl | —CH₂-(1-naphthyl) | 141–144 |
| 1.8 | (S) | N(CH₃)₂ | 2-Me-2-propyl | —CH₂-(1-naphthyl) | |
| 1.9 | (S) | ethyl | ethyl | —CH₂-(1-naphthyl) | |
| 1.10 | (R, S) | ethyl | cyclohexyl | | |
| 1.11 | (R, S) | ethyl | cyclopropyl | —CH₂-(1-naphthyl) | |
| 1.12 | (S) | ethyl | 2-butyl | —CH₂-(5-chloro-2-thienyl) | 131–134 |
| 1.13 | (S) | ethyl | 2-MeS-ethyl | —CH₂-(5-chloro-2-thienyl) | 104–106 |

TABLE 1-continued

[Structure: R₁-S(O)₂-HN-CH(R₂)-C(O)-HN-CH₂CH₂-phenyl(4-O-R₃, 3-OCH₃)]

| Comp. No. | Conf. at α-C | R₁ | R₂ | R₃ | Phys. data m.p. °C |
|---|---|---|---|---|---|
| 1.14 | (S) | propyl | 2-propyl | —CH₂-(5-chloro-thiophen-2-yl) | 130–131 |
| 1.15 | (S) | isopropyl | 1-OH-ethyl | —CH₂-(5-chloro-thiophen-2-yl) | 109–112 |
| 1.16 | (S) | 2-Me-2-propen-1-yl | 2-propyl | —CH₂-(5-chloro-thiophen-2-yl) | 135–137 |
| 1.17 | (S) | N(CH₃)₂ | 2-propyl | —CH₂-(5-chloro-thiophen-2-yl) | 120–121 |

Example 2.1

(S)-2-(Ethylsulfonylamino)-3-methyl-butyric acid N-{2-[4-(5-chloro-thiophen-2-ylmethoxy)-3-methoxy-phenyl]-ethyl}-amide

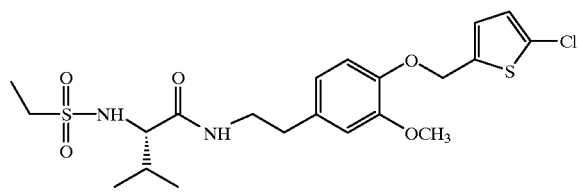

A mixture of 2.0 g of (S)-2-(ethylsulfonylamino)-3methyl-butyric acid N-[2-(4hydroxy-3-methoxy-phenyl)-ethyl]-amide, 1.2 g of 2-chloro-5-chloromethylthiophene and 12 ml of a 1 M sodium methanolate solution in methanol (prepared beforehand by dissolution of 23 g of sodium in 1 liter of methanol) is heated at reflux in 30 ml of methanol for 16 hours. After cooling, the reaction mixture is introduced into 300 ml of 2N sodium hydroxide solution. Extraction is carried out twice using 400 ml of tert-butyl methyl ether each time. The organic phases are washed once with 100 ml of 2N sodium hydroxide solution and once with 100 ml of saturated sodium chloride solution, dried over magnesium sulfate and concentrated, yielding (S)-2-(ethylsulfonylamino)-3-methyl-butyric acid N-{2-[4-(5-chloro-thiophen-2-yl-methoxy)-3-methoxy-phenyl]-ethyl}-amide, which can be purified by chromatography on silica gel with ethyl acetate/n-hexane 1:1 and recrystallisation from ethyl acetate/n-hexane, m.p. 124–127° C.

The Examples listed in Table 2 are obtained in an analogous manner.

TABLE 2

[Structure: R₁-S(O)ₙ-NH-C(R₂)(R₃)-C(O)-NH-CH(R₄)-CH₂-phenyl(4-O-(R₉)p-A, 3-OCH₃)]

| No. | Conf. α-C | n | R₁ | R₂ | R₃ | R₄ | -(R₉)p-A | Phys. data m.p. °C |
|---|---|---|---|---|---|---|---|---|
| 2.1. | (S) | 1 | ethyl | H | 2-propyl | H | —CH₂-(5-chloro-thiophen-2-yl) | 124–127 |
| 2.2. | (S) | 1 | methyl | H | 2-propyl | H | —CH₂-(5-chloro-thiophen-2-yl) | 125–145 |

TABLE 2-continued

| No. | Conf. α-C | n | R₁ | R₂ | R₃ | R₄ | -(R₉)p-A | Phys. data m.p. ° C. |
|---|---|---|---|---|---|---|---|---|
| 2.3. | (S) | 1 | methyl | H | 2-propyl | CH₃ | CH₂-(2,5-thienyl)-Cl | |
| 2.5. | (S) | 1 | trifluoromethyl | H | 2-propyl | H | -CH₂-(2,5-thienyl)-Cl | |
| 2.6. | (S) | 1 | propyl | H | 2-propyl | H | CH₂-(2,5-thienyl)-Cl | |
| 2.7. | (S) | 0 | 2-propyl | H | 2-propyl | H | CH₂-(2,5-thienyl)-Cl | |
| 2.8. | (S) | 1 | 2-propyl | H | 2-propyl | H | -CH₂-(2,5-thienyl)-Cl | |
| 2.9. | (S) | 1 | 2-butyl | H | 2-propyl | H | -CH₂-(2,5-thienyl)-Cl | |
| 2.10. | (S) | 0 | cyclohexyl | H | 2-propyl | H | -CH₂-(2,5-thienyl)-Cl | |
| 2.11. | (S) | 1 | 3-chloropropyl | H | 2-propyl | H | -CH₂-(2,5-thienyl)-Cl | |
| 2.12. | (S) | 1 | N(CH₃)₂ | H | 2-propyl | H | -CH₂-(2,5-thienyl)-Cl | |
| 2.13. | (S) | 1 | NH(CH₃) | H | 2-propyl | H | -CH₂-(2,5-thienyl)-Cl | |
| 2.14. | (S) | 1 | ethyl | H | ethyl | H | -CH₂-(2,5-thienyl)-Cl | |
| 2.15. | (S) | 1 | methyl | H | ethyl | H | -CH₂-(2,5-thienyl)-Cl | |
| 2.16. | (R, S) | 1 | ethyl | H | cyclopropyl | H | -CH₂-(2,5-thienyl)-Cl | 107–109 |
| 2.17. | (R, S) | 1 | ethyl | H | allyl | H | -CH₂-(2,5-thienyl)-Cl | |
| 2.18. | (S) | 1 | ethyl | tetramethylene | | H | -CH₂-(2,5-thienyl)-Cl | |
| 2.19. | (S) | 0 | 2-butyl | H | 2-propyl | H | -CH₂-(2,5-thienyl)-Cl | |

TABLE 2-continued
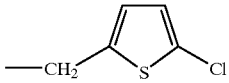
| No. | Conf. α-C | n | R₁ | R₂ | R₃ | R₄ | -(R₉)p-A | Phys. data m.p. ° C. |
|---|---|---|---|---|---|---|---|---|
| 2.20. | (S) | 1 | ethyl | H | 2-butyl | H | 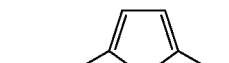 | |
| 2.21. | (R, S) | 1 | ethyl | H | cyclopropylmethyl | H | 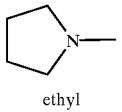 | |
| 2.22. | (S) | 1 | CH₂=C(CH₃)—CH₂ | H | 2-propyl | H | 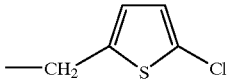 | |
| 2.23. | (S) | 1 | 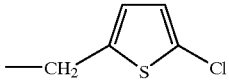 | H | 2-propyl | H | 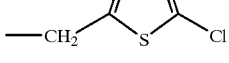 | |
| 2.24. | (S) | 1 | ethyl | H | methyl | H | 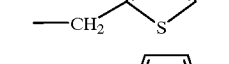 | |
| 2.25. | (S) | 1 | octyl | H | 2-propyl | H | 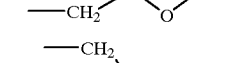 | |
| 2.26. | (S) | 1 | ethyl | H | 2-propyl | H | 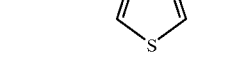 | |
| 2.27. | (S) | 1 | ethyl | H | 2-propyl | H | 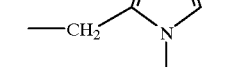 | |
| 2.28. | (S) | 1 | ethyl | H | 2-propyl | H | 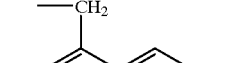 | |
| 2.29. | (S) | 1 | ethyl | H | 2-propyl | H | 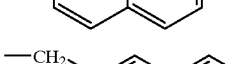 | |
| 2.30. | (S) | 1 | ethyl | H | 2-propyl | H | 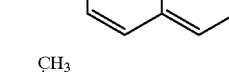 | 134–137 |
| 2.31. | (S) | 1 | ethyl | H | 2-propyl | H | | 126–128 |
| 2.32. | (S) | 1 | ethyl | H | 2-propyl | H | | |

TABLE 2-continued
| No. | Conf. α-C | n | $R_1$ | $R_2$ | $R_3$ | $R_4$ | $-(R_9)_p-A$ | Phys. data m.p. °C. |
|---|---|---|---|---|---|---|---|---|
| 2.33. | (S) | 1 | ethyl | H | 2-propyl | H | 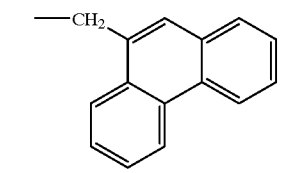 | |
| 2.34. | (S) | 1 | ethyl | H | 2-propyl | H | 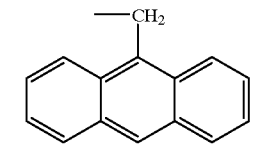 | |
| 2.35 | (S) | 1 | ethyl | H | 2-propyl | H | 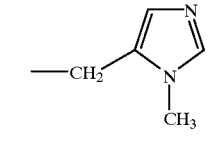 | |
| 2.36. | (S) | 1 | ethyl | H | 2-propyl | H | 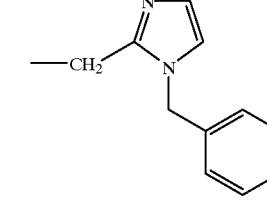 | |
| 2.37. | (S) | 1 | ethyl | H | 2-propyl | H | 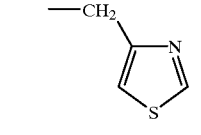 | |
| 2.38. | (S) | 1 | ethyl | H | 2-propyl | H | 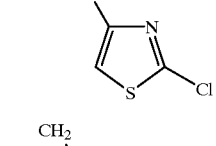 | |
| 2.39. | (S) | 1 | ethyl | H | 2-propyl | H | 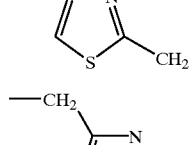 | 123–126 |
| 2.40. | (S) | 1 | ethyl | H | 2-propyl | H | 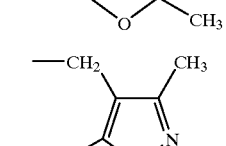 | |
| 2.41. | (S) | 1 | ethyl | H | 2-propyl | H |  | 126–132 |

TABLE 2-continued
| No. | Conf. α-C | n | R₁ | R₂ | R₃ | R₄ | -(R₉)p-A | Phys. data m.p. °C. |
|---|---|---|---|---|---|---|---|---|
| 2.42. | (S) | 1 | ethyl | H | 2-propyl | H | 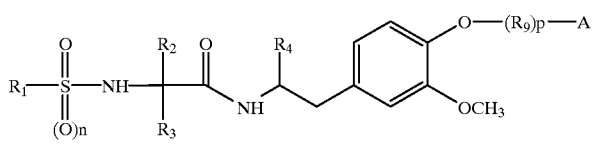 | |
| 2.43. | (S) | 1 | ethyl | H | 2-propyl | H | 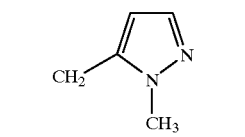 | |
| 2.44. | (S) | 1 | ethyl | H | 2-propyl | H | 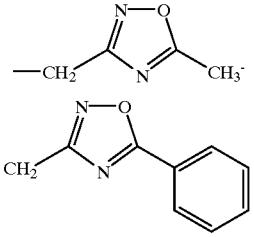 | 118–121 |
| 2.45. | (S) | 1 | ethyl | H | 2-propyl | H | 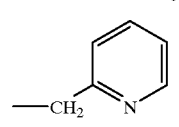 | 134–137 |
| 2.46. | (S) | 1 | ethyl | H | 2-propyl | H | 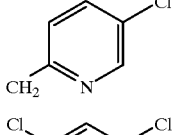 | |
| 2.47. | (S) | 1 | ethyl | H | 2-propyl | H | 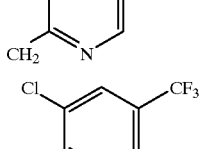 | |
| 2.48. | (S) | 1 | ethyl | H | 2-propyl | H | 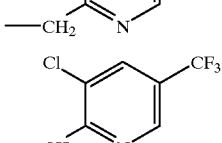 | 141–144 |
| 2.49. | (S) | 1 | methyl | H | 2-propyl | H | 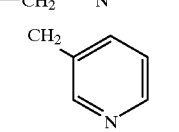 | 130–135 |
| 2.50. | (S) | 1 | ethyl | H | 2-propyl | H | 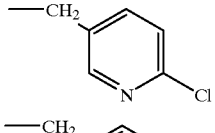 | 141–143 |
| 2.51. | (S) | 1 | ethyl | H | 2-propyl | H | 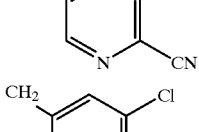 | 168–171 |
| 2.52. | (S) | 1 | ethyl | H | 2-propyl | H | 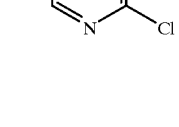 | |
| 2.53. | (S) | 1 | ethyl | H | 2-propyl | H |  | |

TABLE 2-continued
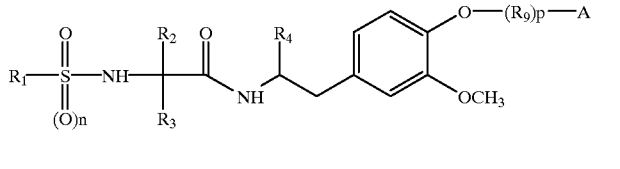
| No. | Conf. α-C | n | R₁ | R₂ | R₃ | R₄ | -(R₉)p-A | Phys. data m.p. ° C. |
|---|---|---|---|---|---|---|---|---|
| 2.54. | (S) | 1 | ethyl | H | 2-propyl | H | 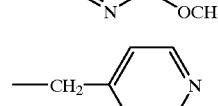 | |
| 2.55. | (S) | 1 | ethyl | H | 2-propyl | H | 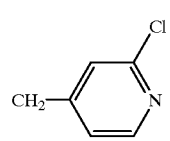 | 152–155 |
| 2.56. | (S) | 1 | ethyl | H | 2-propyl | H | 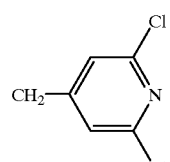 | |
| 2.57. | (S) | 1 | ethyl | H | 2-propyl | H | 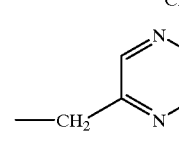 | 142–145 |
| 2.58. | (S) | 1 | ethyl | H | 2-propyl | H | 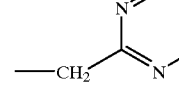 | |
| 2.59. | (S) | 1 | ethyl | H | 2-propyl | H | 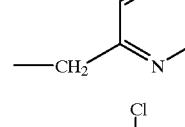 | |
| 2.60. | (S) | 1 | ethyl | H | 2-propyl | H | 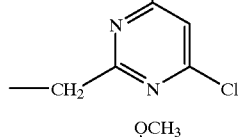 | |
| 2.61. | (S) | 1 | ethyl | H | 2-propyl | H | 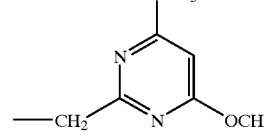 | |
| 2.62. | (S) | 1 | ethyl | H | 2-propyl | H | 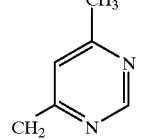 | |
| 2.63. | (S) | 1 | ethyl | H | 2-propyl | H | | |

TABLE 2-continued
| No. | Conf. α-C | n | R₁ | R₂ | R₃ | R₄ | -(R₉)p-A | Phys. data m.p. ° C. |
|---|---|---|---|---|---|---|---|---|
| 2.64. | (S) | 1 | ethyl | H | 2-propyl | H | 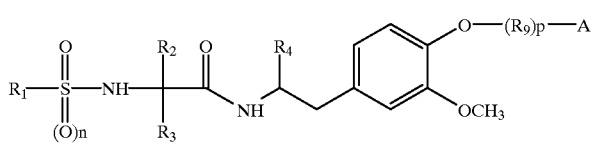 | |
| 2.65. | (S) | 1 | ethyl | H | 2-propyl | H | 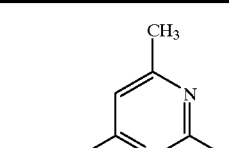 | |
| 2.66. | (S) | 1 | ethyl | H | 2-propyl | H | 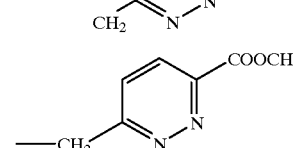 | |
| 2.67. | (S) | 1 | ethyl | H | 2-propyl | H | 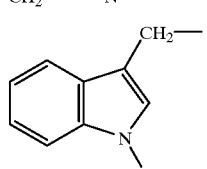 | |
| 2.68. | (S) | 1 | ethyl | H | 2-propyl | H | 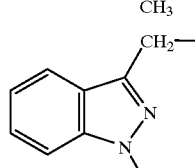 | |
| 2.69. | (S) | 1 | ethyl | H | 2-propyl | H | 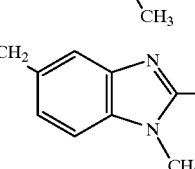 | |
| 2.70. | (S) | 1 | ethyl | H | 2-propyl | H | 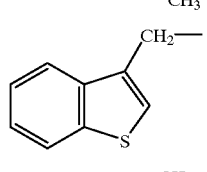 | |
| 2.71. | (S) | 1 | ethyl | H | 2-propyl | H | 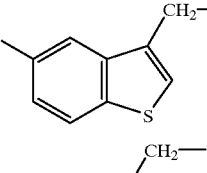 | 152–154 |
| 2.72. | (S) | 1 | ethyl | H | 2-propyl | H | 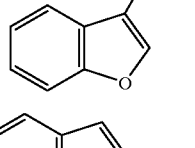 | |
| 2.73. | (S) | 1 | ethyl | H | 2-propyl | H | 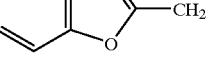 | |

TABLE 2-continued
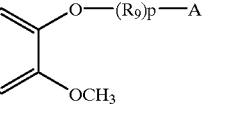
| No. | Conf. α-C | n | R₁ | R₂ | R₃ | R₄ | -(R₉)p-A | Phys. data m.p. ° C. |
|---|---|---|---|---|---|---|---|---|
| 2.74. | (S) | 1 | ethyl | H | 2-propyl | H | 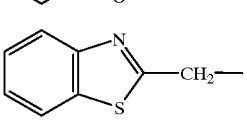 | |
| 2.75. | (S) | 1 | ethyl | H | 2-propyl | H | 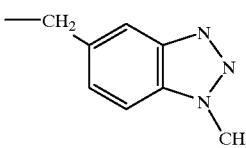 | |
| 2.76. | (S) | 1 | ethyl | H | 2-propyl | H | 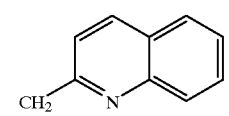 | |
| 2.77. | (S) | 1 | ethyl | H | 2-propyl | H | 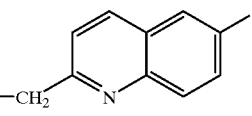 | 133–136 |
| 2.78. | (S) | 1 | ethyl | H | 2-propyl | H | 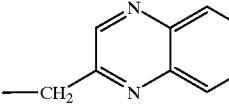 | |
| 2.79. | (S) | 1 | ethyl | H | 2-propyl | H | 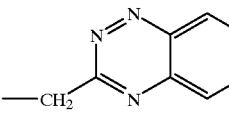 | |
| 2.80. | (S) | 1 | ethyl | H | 2-propyl | H | 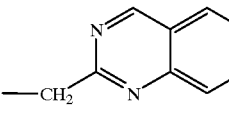 | |
| 2.81. | (S) | 1 | ethyl | H | 2-propyl | H | 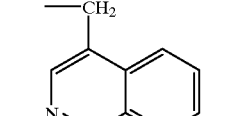 | |
| 2.82. | (S) | 1 | ethyl | H | 2-propyl | H | 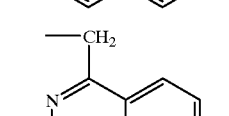 | |
| 2.83 | (S) | 1 | ethyl | H | 2-propyl | H | 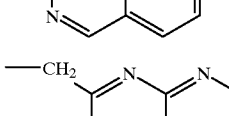 | |
| 2.84 | (S) | 1 | ethyl | H | 2-propyl | H |  | |

TABLE 2-continued

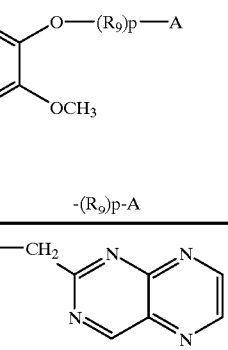

| No. | Conf. α-C | n | R₁ | R₂ | R₃ | R₄ | -(R₉)p-A | Phys. data m.p. °C. |
|---|---|---|---|---|---|---|---|---|
| 2.85 | (S) | 1 | ethyl | H | 2-propyl | H | 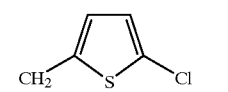 | |
| 2.86 | (S) | 1 | ethyl | H | 2-Me-2-propyl | H | 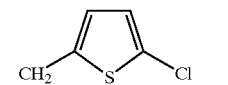 | oil |
| 2.87 | (R, S) | 1 | ethyl | H | cyclo-hexyl | H | 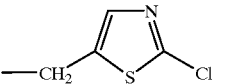 | 147–148 |
| 2.88 | (S) | 1 | ethyl | H | 2-propyl | H | 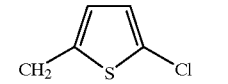 | 151–152 |
| 2.89 | (S) | 1 | ethyl | H | 2-propyl | H | 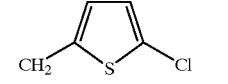 | oil |
| 2.90 | (S) | 1 | ethyl | H | ethyl | H | 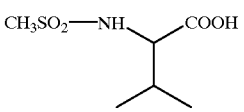 | 171–178 |

Example 3.1

(2S,3S)-2-(Butylsulfonyl-amino)-3methyl-valeric acid N-{2-[3methoxy-4-(naphthalen-1-yl-methoxy)-phenyl]-ethyl}-amide

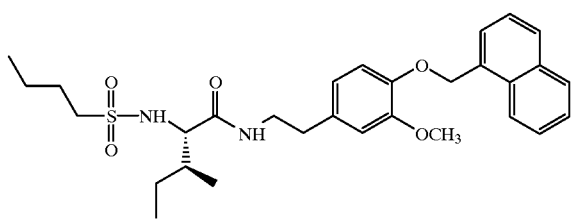

3.4 g of (2S,3S)-2-amino-3-methyl-valeric acid N-{2-[3-methoxy-4-(naphthalen-1-ylmethoxy)-phenyl]-ethyl}-amide and 1.2 ml of triethylamine are placed in 50 ml of dioxane at room temperature. 1.0 ml of n-butylsulfonyl chloride is added thereto. Stirring is carried out for 16 hours. The reaction mixture is introduced into 200 ml of water. Extraction is carried out twice using 200 ml of ethyl acetate each time. The organic phases are washed once with 200 ml of saturated sodium chloride solution, combined, dried over magnesium sulfate and concentrated, yielding (2S,3S)-2-(butylsulfonyl-amino)-3-methyl-valeric acid N-{2-[3-methoxy-4-(naphthalen-1-ylmethoxy)-phenyl]ethyl}-amide, which can be purified by chromatography on silica gel with ethyl acetatein-hexane =1:1, in the form of an oil.

Preparation Example for Intermediates:

Example 5.1.
(R,S)-Methanesulfonic acid N-(2-methyl-1-carboxy)-propyl-amide

CH₃SO₂—NH—CH(COOH)—CH(CH₃)₂

30 g of D,L-valine and 10.2 g of sodium hydroxide are dissolved in 250 ml of water and, with stirring, cooled to 0° C. There are then added dropwise to that solution, simultaneously over a period of one hour, a solution of 10.2 g of sodium hydroxide in 250 ml of water and a solution of 20 ml of methanesulfonic acid chloride in 250 ml of toluene. Stirring of the reaction mixture is continued first at 0° C. for 2 hours and then at room temperature for 16 hours. The toluene phase is then separated off in a separating funnel and discarded. The aqueous phase is adjusted to pH <3 with conc. hydrochloric acid. Extraction is carried out twice using 1000 ml of diethyl ether each time. The organic phases are washed twice using 200 ml of saturated sodium chloride solution each time, combined, dried over magnesium sulfate and concentrated, yielding (R,S)-methanesulfonic acid N-(2-methyl-1-carboxy)-propylamide, which can be purified by recrystallisation from ethyl acetate/hexane, m.p. 90–91° C.

The Examples listed in Table 5 are obtained analogously to the above Example.

TABLE 5

$$R_1 \underset{(O)_n}{\overset{O}{\underset{\|}{S}}} \underset{NH}{\overset{R_2}{\underset{R_3}{C}}} COOH$$

| No. | n | R₁ | R₂ | R₃ | Conf. α-C | Phys. data m.p. °C |
|---|---|---|---|---|---|---|
| 5.1 | 1 | methyl | H | 2-propyl | (R, S) | 90–91 |
| 5.2 | 1 | methyl | H | 2-propyl | (S) | oil |
| 5.3 | 1 | Me₂N- | H | 2-propyl | (R, S) | oil |
| 5.4 | 1 | Me₂N | H | 2-propyl | (S) | resin |
| 5.5 | 0 | methyl | H | 2-propyl | (R, S) | |
| 5.6 | 0 | 2-propyl | H | 2-propyl | (R, S) | |
| 5.7 | 0 | 2-methyl-2-propyl | H | 2-propyl | (R, S) | |
| 5.8 | 0 | methyl | H | 2-propyl | (S) | |
| 5.9 | 0 | 2-propyl | H | 2-propyl | (S) | |
| 5.10 | 0 | 2-methyl-2-propyl | H | 2-propyl | (S) | |
| 5.11 | 0 | cyclohexyl | H | 2-propyl | (S) | |
| 5.12 | 1 | ethyl | H | 2-propyl | (S) | resin |
| 5.13 | 1 | Me₂N | H | 2-butyl | (S) | resin |
| 5.14 | 1 | ethyl | H | 1-(tert-butyl)-oxy-ethyl | (S) | oil |
| 5.15 | 1 | methyl | H | ethyl | (S) | resin |
| 5.18 | 1 | ethyl | H | ethyl | (S) | resin |
| 5.17 | 1 | methyl | methyl | methyl | — | 109–111 |
| 5.18 | 1 | methyl | tetra-methylene | | | |
| 5.19 | 1 | propyl | H | 2-propyl | (S) | oil |
| 5.20 | 1 | 2-propyl | H | 2-propyl | (S) | oil |
| 5.21 | 1 | 3-chloropropyl | H | 2-propyl | (S) | 108–109 |
| 5.22 | 1 | ethenyl | H | 2-propyl | (S) | |
| 5.23 | 1 | butyl | H | 2-propyl | (S) | |
| 5.24 | 1 | isobutyl | H | 2-propyl | (S) | |
| 5.25 | 1 | allyl | H | 2-propyl | (S) | |
| 5.26 | 1 | 2-methyl-2-propen-1-yl | H | 2-propyl | (S) | 120–122 |
| 5.27 | 1 | diethylamino | H | 2-propyl | (S) | |
| 5.28 | 1 | methylamino | H | 2-propyl | (S) | |
| 5.29 | 1 | methyl | H | ethyl | (S) | |
| 5.30 | 1 | ethyl | H | ethyl | (S) | |
| 5.31 | 1 | propy | H | ethyl | (S) | |
| 5.32 | 1 | 2-propyl | H | ethyl | (S) | |
| 5.33 | 1 | dimethylamino | H | ethyl | (S) | |
| 5.34 | 1 | methylamino | H | ethyl | (S) | |
| 5.35 | 1 | ethyl | H | 2-methyl-2-propyl | (S) | 76–78 |
| 5.36 | 1 | ethyl | H | cyclopropyl | (R, S) | oil |
| 5.37 | 1 | ethyl | H | cyclohexyl | (R, S) | oil |

Example 6.1
(S)-2-(Ethylsulfonylamino)-3methyl-butyric acid N-[2-(4-hydroxy-3-methoxy-phenyl)-ethyl]-amide
(S)-2-(Ethylsulfonylamino)-3-methyl-butyric acid N-[2-(4-benzyloxy-3-methoxy-phenyl)-ethyl]-amide

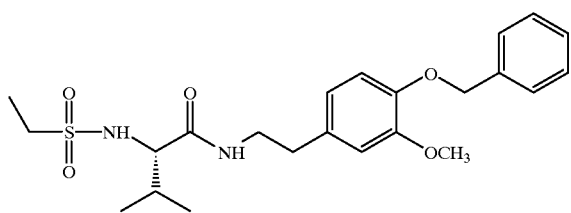

21.1 g of (S)-2-(ethylsulfonylamino)-3-methyl-butyric acid and 12 ml of N-methylmorpholine in 450 ml of tetrahydrofuran are cooled, with stirring, to −20° C. 13.2 ml of isobutyl chloroformate are added dropwise thereto over a period of 10 minutes. The reaction mixture is then stirred at −10° C. for 1 hour. The mixture is again cooled to −20° C., and a solution of 26.1 g of 2-(4-benzyloxy-3-methoxyphenyl)-ethylamine in 100 ml of tetrahydrofuran is added dropwise thereto over a period of 20 minutes. The reaction mixture is then stirred, without cooling, for 4 hours, the internal temperature gradually rising to room temperature. The reaction mixture is then introduced into 400 ml of 2N hydrochloric acid. Extraction is carried out twice using 500 ml of ethyl acetate each time. The organic phases are washed once with 250 ml of 2N hydrochloric acid, once with 250 ml of saturated sodium chloride solution, twice using 250 ml of 2N potassium hydrogen carbonate solution each time and once with 250 ml of saturated sodium chloride solution, dried over magnesium sulfate and concentrated, yielding (S)-2-(ethylsulfonylamino)-3methyl-butyric acid N-[2-(4-benzyloxy-3-methoxy-phenyl)-ethyl]-amide, m.p. 140–142° C., which can be purified further by digestion in 200 ml of tert-butyl methyl ether.

(S)-2-(Ethylsulfonylamino)-3-methyl-butyric acid N-[2-(4-hydroxy-3-methoxy-phenyl)-ethyl]-amide

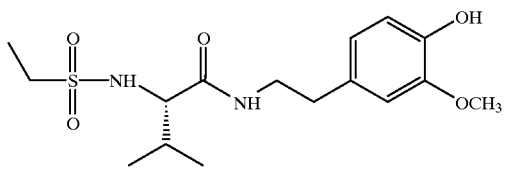

a)

5.1 g of (S)-2-(ethylsulfonylamino)-3-methyl-butyric acid and 5.7 ml of N-methylmorpholine in 200 ml of tetrahydrofuran are cooled, with stirring, to −20° C. 3.15 ml of isobutyl chloroformate are added dropwise thereto. When the addition is complete, the reaction mixture is stirred at −10° C. for 40 minutes. The mixture is again cooled to −20° C. 5.0 g of solid 2-(4-hydroxy-3-methoxy-phenyl)-ethylamine hydrochloride are introduced into the reaction mixture. The reaction mixture is stirred, without cooling, for a further 24 hours, the internal temperature gradually rising to room temperature. The reaction mixture is introduced into 300 ml of 2N hydrochloric acid. Extraction is carried out twice using 500 ml of ethyl acetate each time. The organic phases are washed twice using 100 ml of saturated sodium chloride solution, dried over magnesium sulfate and concentrated. The residue is purified by flash chromatography on silica gel with a mixture of ethyl acetate/n-hexane 3: 1, yielding (S)-2-(ethylsulfonylamino)-3methyl-butyric acid N-[2-(4-hydroxy-3-methoxyphenyl)-ethyl]-amide in the form of a colourless oil.

b)

14.5 g of (S)-2-(ethylsulfonylamino)-3-methyl-butyric acid N-[2-(4-benzyloxy-3-methoxy-phenyl)-ethyl]-amide are dissolved in 420 ml of tetrahydrofuran and, together with 3 g of 5% palladium on active carbon, shaken in a hydrogenation vessel for 5 hours in a hydrogen atmosphere under normal pressure. The catalyst is then filtered off. The filtrate is concentrated. The residue is purified by flash chromatography on silica gel with ethyl acetate/n-hexane 3:1, yielding (S)-2-(ethylsulfonylamino)-3methyl-butyric acid N-[2-(4-hydroxy-3-methoxy-phenyl)-ethyl]-amide in the form of a colourless oil.

c)

1.7 g of 2-(4-hydroxy-3-methoxy-phenyl)-ethylamine and 2.1 g of (S)-2-(ethylsulfonylamino)-3-methyl-butyric acid are stirred at room temperature for 2 hours together with 4.6 g of (benzotriazol-1-yl)-tris(dimethylamino)phosphonium hexafluorophosphate and 4.5 ml of diisopropylethylamine in 40 ml of dimethylformamide. The reaction mixture is then introduced into 600 ml of water. Extraction is carried out twice using 400 ml of ethyl acetate each time. The organic phases are washed twice using 300 ml of water each time and once with 200 ml of saturated sodium chloride solution, dried over magnesium sulfate and concentrated, yielding (S)-2-(ethylsulfonylamino)3-methyl-butyric acid N-[2-(4-hydroxy-3-methoxyphenyl)-ethyl]-amide in the form of a brown oil, which can be purified by chromatography on silica gel with ethyl acetate.

The Examples listed in Table 6 are obtained analogously to the above Example.

TABLE 6

| No. | $R_1$ | $R_3$ | Conf. α-C | Physical data |
|---|---|---|---|---|
| 6.1 | ethyl | 2-propyl | (S) | oil |
| 6.2 | ethenyl | 2-propyl | (S) | |
| 6.3 | methyl | 2-propyl | (S) | m.p. 149–151° C. |
| 6.4 | propyl | 2-propyl | (S) | oil |
| 6.5 | isopropyl | 2-propyl | (S) | oil |
| 6.6 | butyl | 2-propyl | (S) | |
| 6.7 | isobutyl | 2-propyl | (S) | |
| 6.8 | allyl | 2-propyl | (S) | |
| 6.9 | 2-methyl-2-propen-1-yl | 2-propyl | (S) | oil |
| 6.10 | 3-chloropropyl | 2-propyl | (S) | m.p. 124–126° C. |
| 6.11 | dimethylamino | 2-propyl | (S) | |
| 6.12 | diethylamino | 2-propyl | (S) | |
| 6.13 | methylamino | 2-propyl | (S) | |
| 6.14 | methyl | ethyl | (S) | |
| 6.15 | ethyl | ethyl | (S) | oil |
| 6.16 | propyl | ethyl | (S) | |
| 6.17 | isopropyl | ethyl | (S) | |
| 6.18 | dimethylamino | ethyl | (S) | |
| 6.19 | methylamino | ethyl | (S) | |
| 6.19 | methylamino | ethyl | (S) | |
| 6.20 | ethyl | 2-methyl-2-propyl | (S) | resin |
| 6.21 | ethyl | cyclopropyl | (R, S) | resin |
| 6.22 | ethyl | cyclohexyl | (R, S) | resin |
| 6.23 | cyclopropyl | 2-propyl | (S) | oil |

Example 7.7

2-[3-Methoxy-4-(naphthalen-1-ylmethoxy)-phenyl]-ethylamine

3-Methoxy-4-(naphthalen-1-ylmethoxy)-benzaldehyde

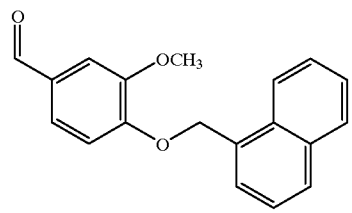

5 g of sodium are dissolved in 200 ml of methanol. 30.4 g of vanillin are metered into the resulting solution. The reaction mixture is stirred at room temperature for 30 minutes. 36 g of 1-chloromethylnaphthalene in 70 ml of methanol are then added and the reaction mixture is heated at reflux for 6 hours. The mixture is left to stand overnight and then introduced into 1 liter of water. Extraction is carried out twice using 700 ml of ethyl acetate each time. The organic phases are washed twice using 200 ml of ice-cold 2N sodium hydroxide solution each time and once with 200 ml of saturated sodium chloride solution, dried over magnesium sulfate and concentrated, yielding 3-methoxy (naphthalen-1-ylmethoxy)-benzaldehyde, which can be purified by chromatography on silica gel with ethyl acetate/n-hexane 1:2 and recrystallisation from ethyl acetate/n-hexane, m.p. 98–99° C.

1-[2-Methoxy-4-(2-nitro-vinyl)-phenoxymethyl]-naththalene

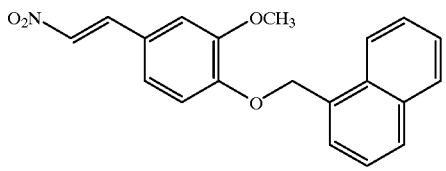

36 g of 3-methoxy-4-(naphthalen-1-ylmethoxy)-benzaldehyde, 8.7 9 of ammonium acetate and 10 ml of nitromethane are together heated at reflux for 5 hours in 140 ml of glacial acetic acid. After cooling, the reaction mixture is introduced into 1.5 liters of water. Extraction is carried out twice using 1 liter of ethyl acetate each time. The organic phases are washed 4 once with 500 ml of water and three times using 400 ml of 2N potassium hydrogen carbonate solution each time, dried over magnesium sulfate and concentrated, yielding 1-[2-methoxy-4-(2-nitro-vinyl)-phenoxymethyl]-naphthalene, which can be purified by chromatography on silica gel with ethyl acetate/n-hexane 1:4 and recrystallisation in ethyl acetate/n-hexane, m.p. 120–123° C.

2-[3-Methoxy-4-(naphthalen-1-ylmethoxy)-phenyl]-ethylamine

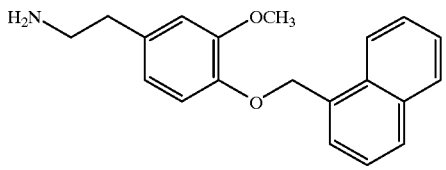

10 g of lithium aluminium hydride are placed in 200 ml of tetrahydrofuran; the mixture is stirred at room temperature. 25.8 g of 1-[2-methoxy-4-(2-nitro-vinyl)-phenoxymethyl]-naphthalene dissolved in 300 ml of tetrahydrofuran are added dropwise thereto over a period of 90 minutes. The reaction mixture is heated at reflux for 4 hours. After cooling, 40 ml of 1 N sodium hydroxide solution are cautiously added dropwise, external cooling being effected using an ice bath. When the addition is complete, the reaction mixture is stirred, without cooling, for one hour, then filtered with suction over Celite and washed with a small amount of tetrahydrofuran. The filtrate is dried over potassium carbonate and concentrated by evaporation, yielding 2-[3-methoxy-4-(naphthalen-1-ylmethoxy)-phenyl]-ethylamine in the form of a brown oil.

The Examples given in Table 7 are obtained analogously to the above Example.

TABLE 7

| Comp. No. | $R_4$ | $-(R_9)_p-A$ | Phys. data |
|---|---|---|---|
| 7.1 | H | —CH$_2$-(2-chloro-thiophen-5-yl) | oil |
| 7.2 | methyl | —CH$_2$-(2-chloro-thiophen-5-yl) | |
| 7.3 | H | —CH$_2$-(thiophen-2-yl) | |
| 7.4 | H | —CH$_2$-(furan-2-yl) | |
| 7.5 | H | —CH$_2$-(thiophen-3-yl) | |
| 7.6 | H | —CH$_2$-(1-methyl-pyrrol-2-yl) | |
| 7.7 | H | —CH$_2$-(naphthalen-1-yl) | |
| 7.8 | H | —CH$_2$-(naphthalen-2-yl) | |
| 7.9 | H | —CH(CH$_3$)-(naphthalen-2-yl) | |
| 7.10 | H | —CH$_2$-(phenanthren-9-yl) | |
| 7.11 | H | —CH$_2$-(anthracen-9-yl) | |

TABLE 7-continued

Structure:

$R_4$ on carbon bearing $H_2N$, attached to benzene ring with $OCH_3$ and $O-(R_9)_p-A$ substituents.

| Comp. No. | $R_4$ | $-(R_9)_p-A$ | Phys. data |
|---|---|---|---|
| 7.12 | H | -CH₂-(1-methylimidazol-5-yl) | |
| 7.13 | H | -CH₂-(1-benzylimidazol-2-yl) | |
| 7.14 | H | -CH₂-(thiazol-4-yl) | |
| 7.15 | H | -CH₂-(2-chlorothiazol-4-yl) | |
| 7.16 | H | -CH₂-(2-methylthiazol-4-yl) | |
| 7.17 | H | -CH₂-(2-methyloxazol-4-yl) | |
| 7.18 | H | -CH₂-(3,5-dimethylisoxazol-4-yl) | |
| 7.19 | H | -CH₂-(1-methylpyrazol-5-yl) | |
| 7.20 | H | -CH₂-(5-methyl-1,3,4-oxadiazol-3-yl) | |
| 7.21 | H | -CH₂-(5-phenyl-1,2,4-oxadiazol-3-yl) | |
| 7.22 | H | -CH₂-(pyridin-2-yl) | |
| 7.23 | H | -CH₂-(5-chloropyridin-2-yl) | |
| 7.24 | H | -CH₂-(3,5-dichloropyridin-2-yl) | |
| 7.25 | H | -CH₂-(3-chloro-5-trifluoromethylpyridin-2-yl) | |
| 7.26 | H | -CH₂-(pyridin-3-yl) | |
| 7.27 | H | -CH₂-(6-chloropyridin-3-yl) | |
| 7.28 | H | -CH₂-(6-cyanopyridin-3-yl) | |
| 7.29 | H | -CH₂-(5,6-dichloropyridin-3-yl) | |
| 7.30 | H | -CH₂-(6-methoxypyridin-3-yl) | |

TABLE 7-continued
| Comp. No. | R4 | -(R9)p-A | Phys. data |
|---|---|---|---|
| 7.31 | H | 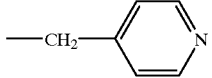 | |
| 7.32 | H | | |
| 7.33 | H | | |
| 7.34 | H | | |
| 7.35 | H | | |
| 7.36 | H | | |
| 7.37 | H | | |
| 7.38 | H | | |
| 7.39 | H | | |
| 7.40 | H | 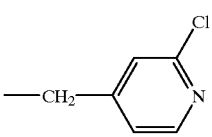 | |
| 7.41 | H | | |
| 7.42 | H | | |
| 7.43 | H | | |
| 7.44 | H | | |
| 7.45 | H | | |
| 7.46 | H | | |
| 7.47 | H | | |

TABLE 7-continued

| Comp. No. | R4 | -(R9)p-A | Phys. data |
|---|---|---|---|
| 7.48 | H | 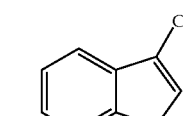 | |
| 7.49 | H | 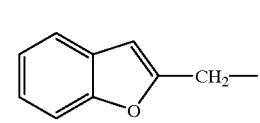 | |
| 7.50 | H | 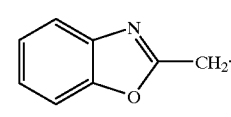 | |
| 7.51 | H | 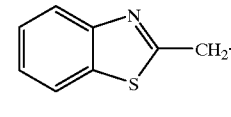 | |
| 7.52 | H | 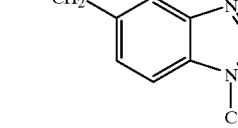 | |
| 7.53 | H | 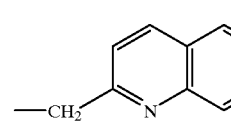 | |
| 7.54 | H | 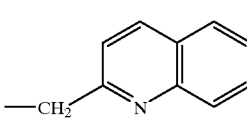 | |
| 7.55 | H | 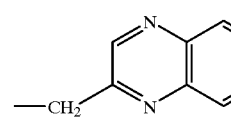 | |
| 7.56 | H | 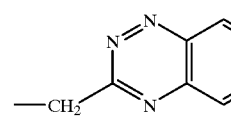 | |
| 7.57 | H | 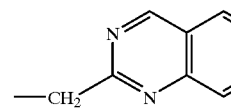 | |
| 7.58 | H | 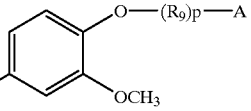 | |
| 7.59 | H | 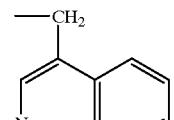 | |
| 7.60 | H | 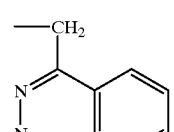 | |
| 7.61 | H | 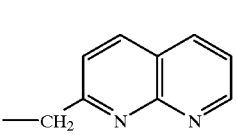 | |

Example 8.16
(2S,3S)-2-Amino-3-methyl-valeric acid N-{2-[3-methoxy-4-(naphthalen-1-ylmethoxy)-phenyl]-ethyl}-amide
(2S,3S)-2-(tert-Butoxycarbonyl-amino)-3methyl-valenic acid N-{2-[3-methoxy-4-(naphthalen-1-ylmethoxy)-phenyl]-ethyl}-amide

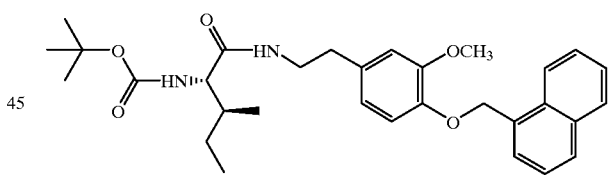

13.9 g of (2S,3S)-2-(tert-butoxycarbonyl-amino)-3-methyl-valeric acid (BOC-L-isoleucine) and 18.5 g of 2-[3-methoxy-4-(naphthalen-1-ylmethoxy)-phenyl]-ethylamine are stirred at room temperature for two hours together with 25 g of (benzotriazol-1-yl)-tris(dimethylamino)-phosphonium hexafluorophosphate and 155 ml of diisopropylethylamine in 300 ml of dimethylformamide. The reaction mixture is then introduced into 800 ml of water. Extraction is carried out twice using 800 ml of ethyl acetate each time. The organic phases are washed twice using 250 ml of 2N hydrochloric acid each time, twice using 250 ml of 2N potassium hydrogen carbonate solution each time and once with 200 ml of saturated sodium chloride solution, dried over magnesium sulfate and concentrated, yielding (2S,3S)-2-(tert-butoxy-carbonyl-amino)-3-methyl-valeric acid N-{2-[3-methoxy-4-(naphthalen-1-ylmethoxy)-phenyl]-ethyl}-amide in the form of a yellowish oil, which can be purified by chromatography on silica gel.

(2S,3S)-2-Amino-3methyl-valeric acid N-{2-[3-methoxy-4-(naphthalen-1-ylmethoxy)-phenyl]-ethyl}-amide

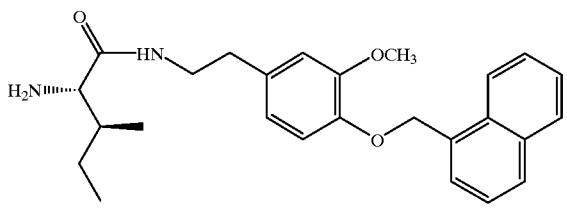

12.6 9 of (2S,3S)-2-(tert-butoxycarbonyl-amino)-3-methyl-valeric acid N-{2-[3-methoxy-4-(naphthalen-1-ylmethoxy)-phenyl]-ethyl}-amide are dissolved in 100 ml of dioxane. 200 ml of a 4M solution of hydrogen chloride in dioxane are added thereto. The reaction mixture is stirred at room temperature for 24 hours and then 300 ml of water are added thereto. Extraction is carried out twice using 300 ml of ethyl acetate each time. The organic phases are washed twice using 150 ml of 2N hydrochloric acid each time. The combined aqueous extracts are adjusted to a pH value of >8 by the addition of solid potassium carbonate. Extraction is carried out twice using 400 ml of tert-butyl methyl ether each time. The organic phases are combined, dried over potassium carbonate and concentrated, yielding (2S,3S)-2-amino-3-methyl-valeric acid N-{2-[3-methoxy-4-(naphthalen-1-ylmethoxy)-phenyl]-ethyl}-amide in the form of a yellow oil.

The Examples given in Table 8 are obtained analogously to the above Example.

TABLE 8

| Comp. No. | Conf at α-C | n | $R_2$ | $R_3$ | $R_4$ | $-(R_9)_p$-A | Phys data |
|---|---|---|---|---|---|---|---|
| 8.1 | (S) | 1 | H | 2-propyl | H | —CH$_2$-thienyl-Cl | |
| 8.2 | (S) | 1 | H | 2-propyl | CH$_3$ | —CH$_2$-thienyl-Cl | |
| 8.3 | (S) | 1 | H | ethyl | H | —CH$_2$-thienyl-Cl | |
| 8.4 | (R, S) | 1 | H | cyclopropyl | H | —CH$_2$-thienyl-Cl | |
| 8.5 | (R, S) | 1 | H | allyl | H | —CH$_2$-thienyl-Cl | |
| 8.6 | (S) | 1 | | | H | —CH$_2$-phthalazinyl | |
| 8.7 | (S) | 1 | H | 2-butyl | H | —CH$_2$-thienyl-Cl | |
| 8.8 | (R, S) | 1 | H | cyclopropyl-methyl | H | —CH$_2$-thienyl-Cl | |

TABLE 8-continued

Structure: H₂N–C(R'₂)(R₃)–C(=O)–NH–CH(R₄)–CH₂–[phenyl with 4-O-(R₉)p–A and 3-OCH₃]

| Comp. No. | Conf at α-C | n | R₂ | R₃ | R₄ | -(R₉)p-A | Phys data |
|---|---|---|---|---|---|---|---|
| 8.9 | (S) | 1 | H | methyl | H | —CH₂-(2-chloro-thien-5-yl) | |
| 8.10 | (S) | 1 | H | 2-propyl | H | —CH₂-(thien-2-yl) | |
| 8.11 | (S) | 1 | H | 2-propyl | H | —CH₂-(furan-2-yl) | |
| 8.12 | (S) | 1 | H | 2-propyl | H | —CH₂-(thien-3-yl) | |
| 8.13 | (S) | 1 | H | 2-propyl | H | —CH₂-(1-methyl-pyrrol-2-yl) | |
| 8.14 | (S) | 1 | H | 2-propyl | H | —CH₂-(naphth-1-yl) | |
| 8.15 | (S) | 1 | H | ethyl | H | —CH₂-(naphth-1-yl) | |
| 8.16 | (S) | 1 | H | 2-butyl | H | —CH₂-(naphth-1-yl) | |
| 8.17 | (S) | 1 | H | 2-propyl | H | —CH₂-(naphth-2-yl) | |
| 8.18 | (S) | 1 | H | 2-propyl | H | —CH(CH₃)-(naphth-2-yl) | |

TABLE 8-continued

Structure: H₂N-C(R'₂)(R₃)-C(=O)-NH-CH(R₄)-CH₂-[3-OCH₃-4-(O-(R₉)p-A)-phenyl]

| Comp. No. | Conf at α-C | n | R₂ | R₃ | R₄ | -(R₉)p-A | Phys data |
|---|---|---|---|---|---|---|---|
| 8.19 | (S) | 1 | H | 2-propyl | H | -CH₂-phenanthrenyl | |
| 8.20 | (S) | 1 | H | 2-propyl | H | -CH₂-(9-anthracenyl) | |
| 8.21 | (S) | 1 | H | 2-propyl | H | -CH₂-(1-methylimidazol-5-yl) | |
| 8.22 | (S) | 1 | H | 2-propyl | H | -CH₂-(1-benzylimidazol-2-yl) | |
| 8.23 | (S) | 1 | H | 2-propyl | H | -CH₂-(thiazol-4-yl) | |
| 8.24 | (S) | 1 | H | 2-propyl | H | -CH₂-(2-chlorothiazol-4-yl) | |
| 8.25 | (S) | 1 | H | 2-propyl | H | -CH₂-(2-methylthiazol-4-yl) | |
| 8.26 | (S) | 1 | H | 2-propyl | H | -CH₂-(2-methyloxazol-4-yl) | |

TABLE 8-continued

| Comp. No. | Conf at α-C | n | R$_2$ | R$_3$ | R$_4$ | -(R$_9$)$_p$-A | Phys data |
|---|---|---|---|---|---|---|---|
| 8.27 | (S) | 1 | H | 2-propyl | H | —CH$_2$-(3,5-dimethylisoxazol-4-yl) | |
| 8.28 | (S) | 1 | H | 2-propyl | H | —CH$_2$-(1-methylimidazol-5-yl) | |
| 8.29 | (S) | 1 | H | 2-propyl | H | —CH$_2$-(5-methyl-1,2,4-oxadiazol-3-yl) | |
| 8.30 | (S) | 1 | H | 2-propyl | H | —CH$_2$-(5-phenyl-1,2,4-oxadiazol-3-yl) | |
| 8.31 | (S) | 1 | H | 2-propyl | H | —CH$_2$-(pyridin-2-yl) | |
| 8.32 | (S) | 1 | H | 2-propyl | H | —CH$_2$-(5-chloropyridin-2-yl) | |
| 8.33 | (S) | 1 | H | 2-propyl | H | —CH$_2$-(3,5-dichloropyridin-2-yl) | |
| 8.34 | (S) | 1 | H | 2-propyl | H | —CH$_2$-(3-chloro-5-trifluoromethylpyridin-2-yl) | |
| 8.35 | (S) | 1 | H | 2-propyl | H | —CH$_2$-(pyridin-3-yl) | |
| 8.36 | (S) | 1 | H | 2-propyl | H | —CH$_2$-(6-chloropyridin-3-yl) | |

TABLE 8-continued

| Comp. No. | Conf at α-C | n | R₂ | R₃ | R₄ | -(R₉)p-A | Phys data |
|---|---|---|---|---|---|---|---|
| 8.37 | (S) | 1 | H | 2-propyl | H | —CH₂-(pyridine-2-CN, 5-yl) | |
| 8.38 | (S) | 1 | H | 2-propyl | H | —CH₂-(2,3-dichloropyridin-5-yl) | |
| 8.39 | (S) | 1 | H | 2-propyl | H | —CH₂-(2-methoxypyridin-5-yl) | |
| 8.40 | (S) | 1 | H | 2-propyl | H | —CH₂-(pyridin-4-yl) | |
| 8.41 | (S) | 1 | H | 2-propyl | H | —CH₂-(2-chloropyridin-4-yl) | |
| 8.42 | (S) | 1 | H | 2-propyl | H | —CH₂-(2,6-dichloropyridin-4-yl) | |
| 8.43 | (S) | 1 | H | 2-propyl | H | —CH₂-(pyrazin-2-yl) | |
| 8.44 | (S) | 1 | H | 2-propyl | H | —CH₂-(pyrimidin-2-yl) | |
| 8.45 | (S) | 1 | H | 2-propyl | H | —CH₂-(pyrimidin-4-yl) | |
| 8.46 | (S) | 1 | H | 2-propyl | H | —CH₂-(4,6-dichloropyrimidin-2-yl) | |

TABLE 8-continued

Structure: H₂N-C(R'₂)(R₃)-C(=O)-NH-CH(R₄)-CH₂-[phenyl with 3-OCH₃ and 4-O-(R₉)p-A]

| Comp. No. | Conf at α-C | n | R₂ | R₃ | R₄ | -(R₉)p-A | Phys data |
|---|---|---|---|---|---|---|---|
| 8.47 | (S) | 1 | H | 2-propyl | H | -CH₂-(4,6-dimethoxypyrimidin-2-yl) | |
| 8.48 | (S) | 1 | H | 2-propyl | H | -CH₂-(6-methylpyrimidin-4-yl) | |
| 8.49 | (S) | 1 | H | 2-propyl | H | -CH₂-(2-chloro-6-methylpyrimidin-4-yl) | |
| 8.50 | (S) | 1 | H | 2-propyl | H | -CH₂-(pyridazin-3-yl) | |
| 8.51 | (S) | 1 | H | 2-propyl | H | -CH₂-(6-methoxycarbonylpyridazin-3-yl) | |
| 8.52 | (S) | 1 | H | 2-propyl | H | -CH₂-(1,3-dimethyl-1H-isoindol-3-yl) derivative | |
| 8.53 | (S) | 1 | H | 2-propyl | H | -CH₂-(1-methyl-1H-indazol-3-yl) | |
| 8.54 | (S) | 1 | H | 2-propyl | H | -(1-methyl-2-methylthio-1H-benzimidazol-?-yl) | |

TABLE 8-continued
| Comp. No. | Conf at α-C | n | R₂ | R₃ | R₄ | -(R₉)ₚ-A | Phys data |
|---|---|---|---|---|---|---|---|
| 8.55 | (S) | 1 | H | 2-propyl | H | 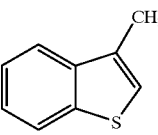 | |
| 8.56 | (S) | 1 | H | 2-propyl | H | 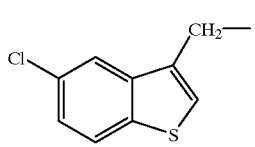 | |
| 8.57 | (S) | 1 | H | 2-propyl | H | 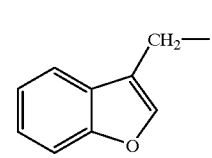 | |
| 8.58 | (S) | 1 | H | 2-propyl | H | 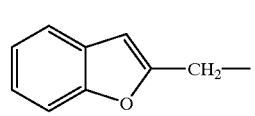 | |
| 8.59 | (S) | 1 | H | 2-propyl | H | 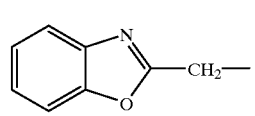 | |
| 8.60 | (S) | 1 | H | 2-propyl | H | 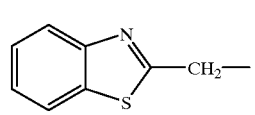 | |
| 8.61 | (S) | 1 | H | 2-propyl | H | 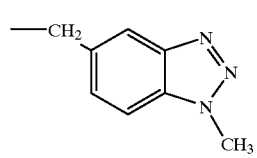 | |
| 8.62 | (S) | 1 | H | 2-propyl | H | 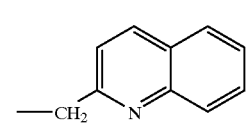 | |
| 8.63 | (S) | 1 | H | 2-propyl | H | 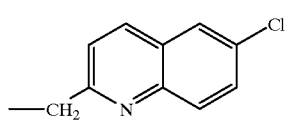 | |
| 8.64 | (S) | 1 | H | 2-propyl | H | 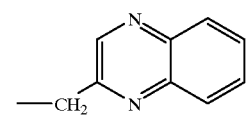 | |

TABLE 8-continued

| Comp. No. | Conf at α-C | n | R₂ | R₃ | R₄ | -(R₉)ₚ-A | Phys data |
|---|---|---|---|---|---|---|---|
| 8.65 | (S) | 1 | H | 2-propyl | H | —CH₂-(benzo[1,2,4]triazin-3-yl) | |
| 8.66 | (S) | 1 | H | 2-propyl | H | —CH₂-(quinazolin-2-yl) | |
| 8.67 | (S) | 1 | H | 2-propyl | H | —CH₂-(isoquinolin-4-yl) | |
| 8.68 | (S) | 1 | H | 2-propyl | H | —CH₂-(phthalazin-1-yl) | |
| 8.69 | (S) | 1 | H | 2-propyl | H | —CH₂-(1,8-naphthyridin-2-yl) | |
| 8.70 | (S) | 1 | H | 2-propyl | H | —CH₂-(pteridin-2-yl) | |

Formulation Examples for Compounds of Formula I (Throughout, Percentages are by Weight)

F-1 : Wettable powders

| | a) | b) | c) |
|---|---|---|---|
| a compound of Tables 1 and 2, e.g. Comp. 2.2 | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| octylphenol polyethylene glycol ether (7–8 mol of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of any desired concentration.

F-2: Emulsifiable concentrate

| | |
|---|---|
| a compound of Tables 1 and 2, e.g. Comp. 2.2 | 10% |
| octylphenol polyethylene glycol ether (4–5 mol of ethylene oxide) | 3% |
| calcium dodecylbenzenesulfonate | 3% |
| castor oil glycol ether (35 mol of ethylene oxide) | 4% |
| cyclohexanone | 30% |
| xylene mixture | 50% |

Emulsions of any required concentration can be obtained from this concentrate by dilution with water.

| F-3: Dusts | | |
|---|---|---|
| | a) | b) |
| a compound of Tables 1 and 2 | 5% | 8% |
| talcum | 95% | — |
| kaolin | — | 92% |

Ready-for-use dusts are obtained by mixing the active ingredient with the carrier and grinding the mixture in a suitable mill.

| F-4: Extruder granules | |
|---|---|
| a compound of Tables 1 and 2 | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| F-5: Coated granules | |
|---|---|
| a compound of Tables 1 and 2 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granules are obtained in this manner.

| F-6: Suspension concentrate | |
|---|---|
| a compound of Tables 1 and 2, e.g. Comp. 2.2 | 40% |
| ethylene glycol | 10% |
| nonylphenol polyethylene glycol ether (15 mol of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired dilution can be obtained by dilution with water.

Biological Examples

B-1: Action against Plasmopara Viticola on Vines a) Residual-protective action

Vine seedlings are sprayed at the 4- to 5leaf stage with a spray mixture (0.02% active ingredient) prepared from a wettable powder formulation of the test compound. After 24 hours, the treated plants are infected with a sporangia suspension of the fungus. Fungus infestation is evaluated after incubation for 6 days at 95–100% relative humidity and 20° C.

b) Residual-curative Action

Vine seedlings are infected at the 4- to 5-leaf stage with a sporangia suspension of the fungus. After incubation for 24 hours in a humidity chamber at 95–100% relative humidity and 20° C., the infected plants are dried and sprayed with a spray mixture (0.02% active ingredient) prepared from a wettable powder formulation of the test compound. After the spray coating has dried, the treated plants are placed in the humidity chamber again. Fungus infestation is evaluated 6 days after infection.

Compounds of Tables 1 to 4 exhibit a very good fungicidal action against Plasmopara viticola on vines. Compounds Nos. inter alia 1.1., 1.7., 1.12., 1.17., 2.1., 2.2., 2.16., 2.30., 2.31. and 2.57 achieve complete suppression of fungus infestation (residual infestation 0 to 5%). On the other hand, Plasmopara infestation on untreated and infected control plants is 100%.

B-2: Action against Phytophthora on Tomato Plants a) Residual-protective Action

After a cultivation period of 3 weeks, tomato plants are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 5 days at 90–100% relative humidity and 20° C.

b) Systemic Action

After a cultivation period of 3 weeks, tomato plants are watered with a spray mixture (0.02% active ingredient based on the volume of the soil) prepared from a wettable powder formulation of the test compound. Care is taken that the spray mixture does not come into contact with the parts of the plants that are above the ground. After 96 hours, the treated plants are infected with a sporangia suspension of the fungus. Fungus infestation is evaluated after incubation of the infected plants for 4 days at 90–100% relative humidity and 20° C. Compounds of Tables 1 and 2 exhibit a lasting effect (less than 20% fungus infestation). Infestation is prevented virtually completely (0 to 5% infestation) with compounds Nos. 1.1., 1.7., 1.12., 1.17., 2.1., 2.2., 2.16., 2.30., 2.31. and 2.57. On the other hand, Phytophthora infestation on untreated and infected control plants is 100%.

B-3: Action against Phytophthora on Potato Plants a) Residual-protective Action

2–3 week old potato plants (Bintje variety) are sprayed with a spray mixture (0.02% active ingredient) prepared from a wettable powder formulation of the test compound. After 48 hours, the treated plants are infected with a sporangia suspension of the fungus. Fungus infestation is evaluated after incubation of the infected plants for 4 days at 90–100% relative humidity and 20° C.

b) Systemic Action

2–3 week old potato plants (Bintje variety) are watered with a spray mixture (0.02% active ingredient based on the volume of the soil) prepared from a wettable powder formulation of the test compound. Care is taken that the spray mixture does not come into contact with the parts of the plants that are above the ground. After 48 hours, the treated plants are infected with a sporangia suspension of the fungus. Fungus infestation is evaluated after incubation of the infected plants for 4 days at 90–100% relative humidity and 20° C.

Compounds of Tables 1 and 2 exhibit a lasting effect (less than 20% fungus infestation). Infestation is prevented virtually completely (0 to 5% infestation) with compounds Nos. 1.1., 1.7., 1.12., 1.17., 2.1., 2.2., 2.16., 2.30., 2.31. and 2.57. On the other hand, Phytophthora infestation on untreated and infected control plants is 100%.

What is claimed is:

1. A compound of formula I:

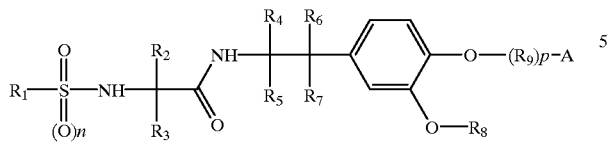

wherein n is a number zero or one; and $R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl, $C_3$–$C_8$cycloalkyl, cyano, $C_1$–$C_6$alkoxycarbonyl, $C_3$–$C_6$alkenyloxycarbonyl, $C_1$–$C_6$alkynyloxycarbonyl; $C_3$–$C_8$cycloalkyl; $C_2$–$C_{12}$alkenyl; $C_2$–$C_{12}$alkynyl; $C_1$–$C_{12}$haloalkyl or a group $NR_{11}R_{12}$; wherein $R_{11}$ and $R_{12}$ are each independently of the other hydrogen, $C_1$–$C_6$alkyl or together are tetra- or penta-methylene;

$R_2$ and $R_3$ are each independently of the other hydrogen; $C_1$–$C_8$alkyl; $C_1$–$C_8$alkyl substituted by hydroxy, $C_1$–$C_4$alkoxy, mercapto or by $C_1$–$C_4$alkylthio; $C_3$–$C_8$alkenyl; $C_3$–$C_8$alkynyl; $C_3$–$C_8$cycloalkyl; $C_3$–$C_8$cycloalkyl-$C_1$–$C_4$alkyl or wherein the two groups $R_2$ and $R_3$ together with the carbon atom to which they are bonded form a three- to eight-membered ring;

$R_4$, $R_5$, $R_6$ and $R_7$ are identical or different and are each independently of the others hydrogen or $C_1$–$C_4$alkyl;

$R_8$ is $C_1$–$C_6$alkyl, $C_3$–$C_6$alkenyl or $C_3$–$C_6$alkynyl;

p is a number zero or one;

$R_9$ is $C_1$–$C_6$alkylene; and

A is unsubstituted or mono- or poly-substituted heteroaryl or unsubstituted or mono- or poly-substituted aryl containing more than 6 carbon atoms.

2. A compound according to claim 1, wherein:

A is naphthyl, heteroaryl that is formed from one or two five- or six-membered rings and that may contain from 1 to 4 identical or different hetero atoms selected from nitrogen, oxygen and sulfur, wherein that naphthyl or heteroaryl may carry from 1 to 4 identical or different substituents selected from: $C_1$–$C_8$alkyl, $C_2$–$C_8$alkenyl, $C_2$–$C_8$alkynyl, $C_3$–$C_8$cycloalkyl, $C_3$–$C_8$cycloalkyl-$C_1$–$C_4$alkyl, phenyl, phenyl-$C_1$–$C_4$alkyl, it being possible for the hydrogen atoms of those groups to have been replaced by one or more identical or different halogen atoms; $C_1$–$C_8$alkoxy, $C_3$–$C_8$alkenyloxy, $C_3$–$C_8$alkynyloxy, $C_1$–$C_4$alkoxy-$C_1$–$C_4$alkyl, $C_1$–$C_8$haloalkoxy, $C_1$–$C_8$alkylthio, $C_1$–$C_8$haloalkylthio, $C_1$–$C_8$alkylsulfonyl, formyl, $C_2$–$C_8$alkanoyl, hydroxy, halogen, cyano, nitro, amino, $C_1$–$C_8$alkylamino, $C_1$–$C_8$dialkylamino, carboxy, $C_1$–$C_8$alkoxycarbonyl, $C_3$–$C_8$alkenyloxycarbonyl and $C_3$–$C_8$alkynyloxycarbonyl.

3. A compound according to claim 2, wherein:

A is naphthyl, furyl, thienyl, pyrrolyl, imidazolyl, pyrazolyl, thiazolyl, oxazolyl, isoxazolyl, oxadiazolyl, pyridyl, pyridazinyl, pyrimidinyl, pyrazinyl, triazinyl, indolyl, benzothiophenyl, benzofuranyl, benzimidazolyl, benzothiazolyl, benzoxazolyl, quinolinyl, quinoxalinyl, unsubstituted or substituted by from 1 to 3 substituents selected from:

$C_1$–$C_8$alkyl, $C_2$–$C_8$alkenyl, $C_2$–$C_8$alkynyl, $C_3$–$C_8$cycloalkyl, $C_3$–$C_8$cycloalkyl-$C_1$–$C_4$alkyl, phenyl, phenyl-$C_1$–$C_4$alkyl, it being possible for the hydrogen atoms of those groups to have been replaced by one or more identical or different halogen atoms; $C_1$–$C_8$alkoxy, $C_3$–$C_8$alkenyloxy, $C_3$–$C_8$alkynyloxy, $C_1$–$C_4$alkoxy-$C_1$–$C_4$alkyl, $C_1$–$C_8$haloalkoxy, $C_1$–$C_8$alkylthio, $C_1$–$C_8$haloalkylthio, $C_1$–$C_8$alkylsulfonyl, formyl, $C_2$–$C_8$alkanoyl, hydroxy, halogen, cyano, nitro, amino, $C_1$–$C_8$alkylamino, $C_1$–$C_8$dialkylamino, carboxy, $C_1$–$C_8$alkoxycarbonyl, $C_3$–$C_8$alkenyloxycarbonyl and $C_3$–$C_8$alkynyloxycarbonyl.

4. A compound according to claim 3, wherein:

p is a number one;

A is naphthyl, furyl, thienyl, pyrrolyl, imidazolyl, pyrazolyl, thiazolyl, oxazolyl, isoxazolyl, oxadiazolyl, thiazolyl, pyridyl, pyridazinyl, pyrimidinyl, pyrazinyl, triazinyl, indolyl, benzothiophenyl, benzofuranyl, benzimidazolyl, benzothiazolyl, benzoxazolyl, quinolinyl, quinoxalinyl, unsubstituted or substituted by from 1 to 3 substituents selected from:

$C_1$–$C_8$alkyl, $C_1$–$C_8$haloalkyl, phenyl, phenyl-$C_1$–$C_4$alkyl, $C_1$–$C_8$alkoxy, $C_1$–$C_8$haloalkoxy, $C_1$–$C_8$alkylthio, $C_1$–$C_8$haloalkylthio, halogen, cyano and nitro.

5. A compound according to claim 4, wherein:

$R_9$ is —$CH_2$—;

A is naphthyl, furyl, thienyl, thiazolyl, oxazolyl, pyridyl, pyridazinyl, pyrimidinyl, pyrazinyl, triazinyl, unsubstituted or substituted by from 1 to 3 substituents selected from:

$C_1$–$C_8$alkyl, $C_1$–$C_8$haloalkyl, phenyl, phenyl-$C_1$–$C_4$alkyl, $C_1$–$C_8$alkoxy, $C_1$–$C_8$haloalkoxy, $C_1$–$C_8$alkylthio, $C_1$–$C_8$haloalkylthio, halogen, cyano and nitro.

6. A compound according to claim 3, wherein:

n is a number one, $R_1$ is $C_1$–$C_{12}$alkyl that is unsubstituted or may be substituted by $C_1$–$C_4$alkoxy, $C_1$–$C_4$alkylthio, $C_1$–$C_4$alkylsulfonyl; $C_2$–$C_{12}$alkenyl; $C_2$–$C_{12}$alkynyl; $C_1$–$C_{12}$haloalkyl or a group $NR_{11}R_{12}$;

wherein $R_{11}$ and $R_{12}$ are each independently of the other hydrogen, $C_1$–$C_6$alkyl or together are tetra- or penta-methylene;

$R_2$ is hydrogen;

$R_3$ is $C_1$–$C_8$alkyl; $C_1$–$C_8$alkyl substituted by hydroxy, $C_1$–$C_4$alkoxy, mercapto or by $C_1$–$C_4$alkylthio; $C_3$–$C_8$alkenyl; $C_3$–$C_8$alkynyl; $C_3$–$C_8$cycloalkyl; $C_3$–$C_8$cycloalkyl-$C_1$–$C_4$alkyl.

7. A compound according to claim 6, wherein:

$R_1$ is $C_1$–$C_4$alkyl or dimethylamino;

$R_3$ is $C_3$–$C_4$alkyl;

$R_4$ is hydrogen or methyl;
$R_8$ is $C_1$–$C_2$alkyl.

8. A process for the preparation of a compound of formula I according to claim 1, which process comprises a) reacting a substituted amino acid of formula II

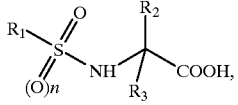
II wherein the radicals $R_1$, $R_2$ and $R_3$ and n are as defined in claim 1, or a carboxy-activated 4 derivative thereof, if desired in the presence of a catalyst, if desired in the presence of an acid-binding agent and if desired in the presence of a diluent, at temperatures of from −80 to +150° C., with an amine of formula III

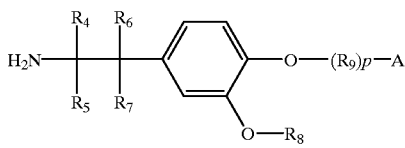
III wherein $R_4$, $R_5$, $R_6$, $R_7$, $R_8$, $R_9$, p and A are as defined in claim 1; or b) oxidising a compound of formula I'

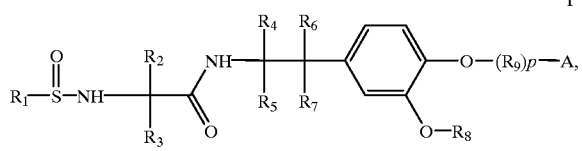
I' wherein $R_4$, $R_5$, $R_6$, $R_7$, $R_8$, $R_9$, p and A are as defined in claim 1, with the proviso that none of the substituents $R_1$, $R_2$, $R_3$ and A contains a thiol or alkylthio group, with an oxidising agent, in an inert diluent, optionally in the presence of an acid or optionally in the presence of a base, at temperatures of from −80 to +150° C.; or c) reacting a compound of formula IV

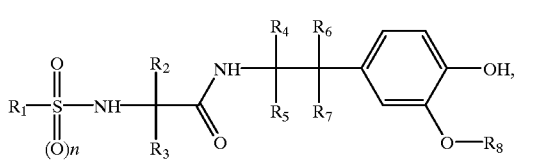
IV wherein $R_1$, $R_2$, $R_3$, $R_4$, $R_5$, $R_6$, $R_7$ and $R_8$ and n are as defined in claim 1, with a compound of formula V Y—(R$_9$)p—A         V, wherein $R_9$, p and A are as defined in claim 1 and wherein Y is a leaving group, in an inert solvent, if desired in the presence of an acid-binding agent, at temperatures of from −80 to +200° C.; or d) reacting a sulfonic acid or sulfinic acid, or a sulfonic acid or sulfinic acid derivative, of formula VI

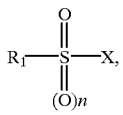
VI wherein $R_1$ and n are as defined in claim 1 and wherein X is an OH group or a leaving group, respectively, with an amine of formula VII

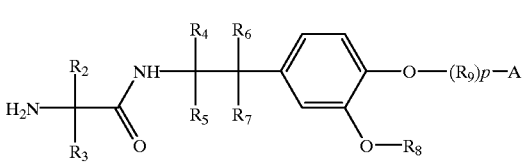
VII wherein $R_2$, $R_3$, $R_4$,l $R_5$, $R_6$, $R_7$, $R_8$, $R_9$, p and A are as defined in claim 1, in an inert solvent, if desired in the presence of an acid-binding agent, at temperatures of from −80 to +150° C.

9. A composition for controlling and preventing pests, comprising a compound according to claim 1 as active ingredient together with a suitable carrier.

10. A method of controlling and preventing an infestation of crop plants by phytopathogenic microorganisms, which comprises the application of a compound of formula I according to claim 1 as active ingredient to the plant, to parts of plants or to the locus thereof.

11. A method according to claim 10, wherein the phytopathogenic microorganisms are fungal organisms.

12. A compound of formula III

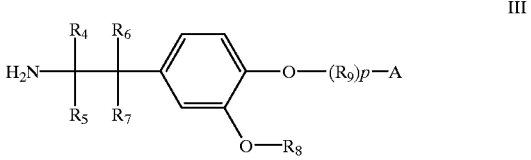
III wherein $R_4$, $R_5$, $R_6$, $R_7$, $R_8$, $R_9$, p and A are as defined in claim 1.

13. A process for the preparation of a compound of formula III according to claim 12, which process comprises using Process variant 1, for $R_4$, $R_5$, $R_6$ and $R_7$ = hydrogen

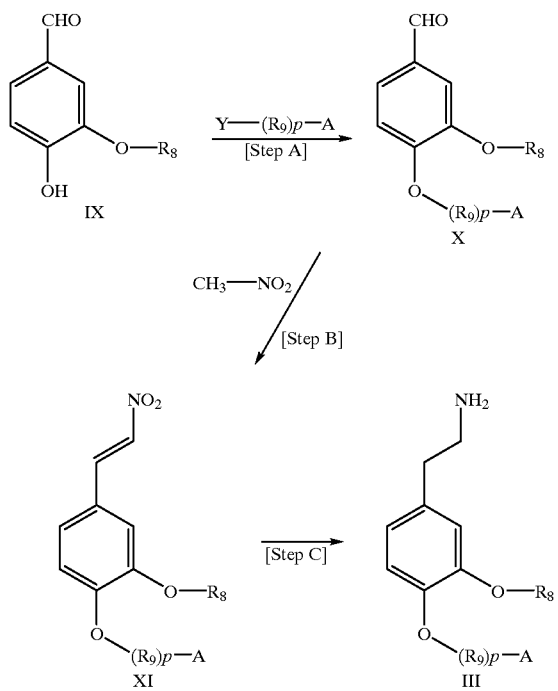

Process variant 2

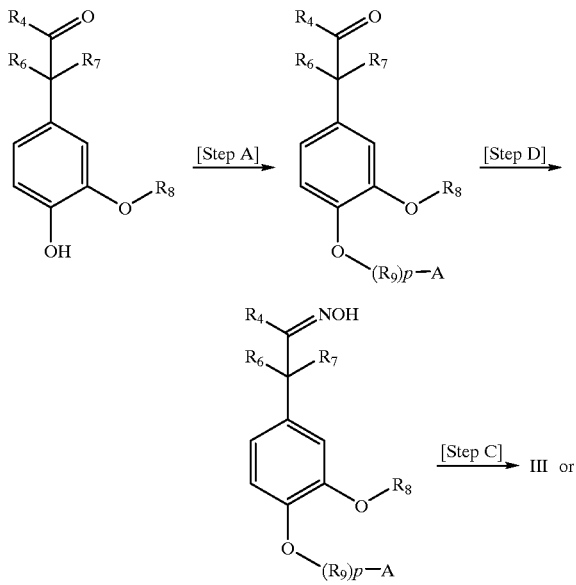

Process variant 3

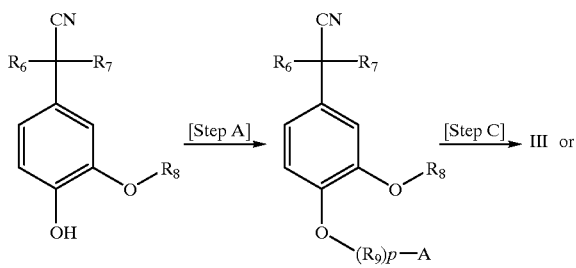

Process variant 4

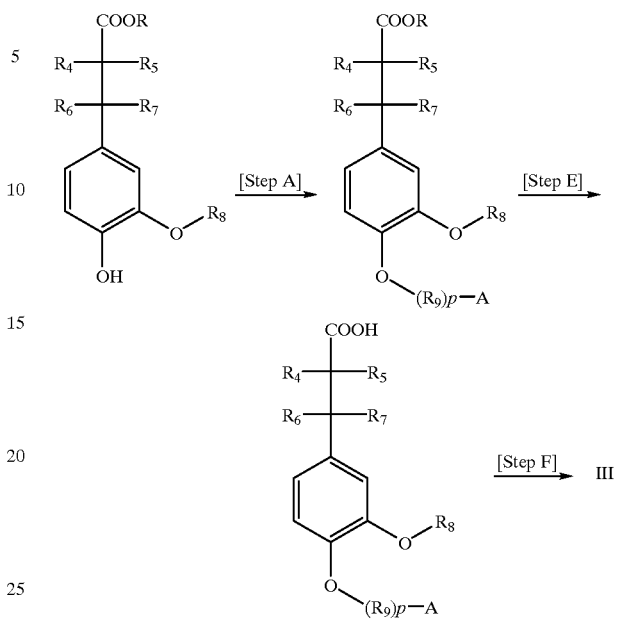

$R = C_1$–$C_5$alkyl wherein

Step A is the alkylation of a phenol with a compound of formula V;

Step B is the reaction of an aromatic aldehyde with nitromethane;

Step C is the reduction of an unsaturated nitrogen compound;

Step D is the reaction of an aldehyde or a ketone with hydroxylamine or a hydroxylamine salt;

Step E is the hydrolysis of a lower alkyl ester, and

Step F is the reaction of a carboxylic acid or an activated carboxylic acid derivative with hydrazoic acid or with a salt of that acid.

14. A compound of formula VII

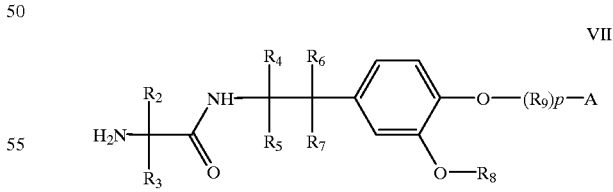

wherein $R_2$, $R_3$, $R_4$, $R_5$, $R_6$, $R_7$, $R_8$, $R_9$, p and A are as define in claim 1.

15. A process for the preparation of a compound of formula VII according to claim 14, which comprises carrying out the following reaction sequence

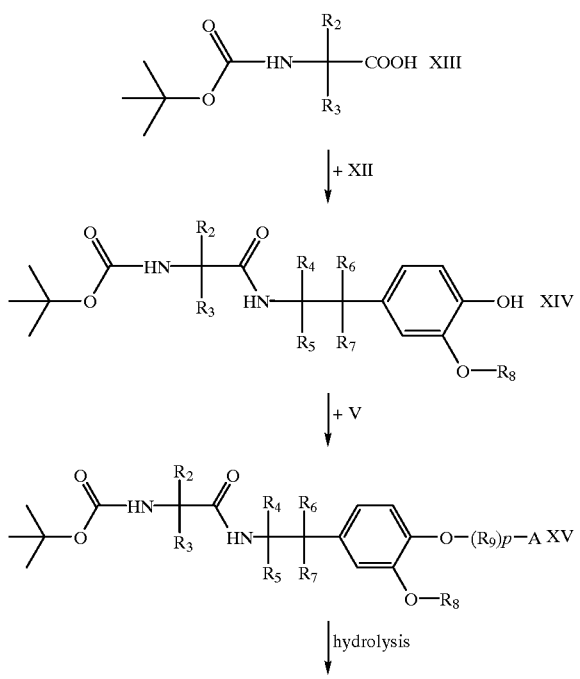

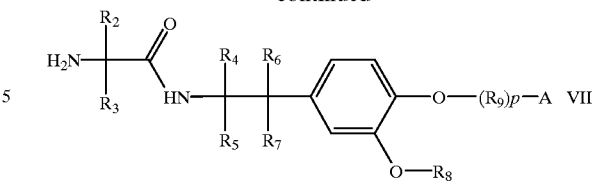

wherein
the reaction of the amino acid derivative of formula XIII, or of a carboxy-activated derivative thereof, with an amine of formula XII is carried out if desired in the presence of a catalyst, if desired in the presence of an acid-binding agent and if desired in the presence of a diluent; and the reaction of a compound of formula XIV with a compound of formula V is carried out if desired in the presence of an acid-binding agent and if desired in the presence of an inert diluent at temperatures of from $-80$ to $+200°$ C.; and then the acid hydrolysis of a compound of formula XV with an inorganic or organic acid is carried out if desired in the presence of an inert diluent, at temperatures of from $-40$ to $+150°$ C.

* * * * *